(12) United States Patent
Craig et al.

(10) Patent No.: US 7,481,781 B2
(45) Date of Patent: Jan. 27, 2009

(54) ULTRASOUND THERAPY

(75) Inventors: Roger Kingdon Craig, Coleraine (GB); Anthony Patrick McHale, Coleraine (GB); Ana Maria Rollan-Haro, Madrid (ES)

(73) Assignee: Gendel Limited, County Londonderry (GB)

( * ) Notice: Subject to any disclaimer, the term of this patent is extended or adjusted under 35 U.S.C. 154(b) by 840 days.

(21) Appl. No.: 10/439,470

(22) Filed: May 16, 2003

(65) Prior Publication Data

US 2003/0229283 A1  Dec. 11, 2003

Related U.S. Application Data

(63) Continuation-in-part of application No. PCT/GB01/05065, filed on Nov. 16, 2001, and a continuation-in-part of application No. 10/113,173, filed on Mar. 29, 2002, now Pat. No. 6,821,274.

(60) Provisional application No. 60/322,588, filed on Sep. 14, 2001, provisional application No. 60/279,812, filed on Mar. 29, 2001.

(51) Int. Cl.
*A61H 1/00* (2006.01)
(52) U.S. Cl. ............................... 601/2; 606/32; 601/15
(58) Field of Classification Search ............. 601/1–5, 601/15; 600/439, 407; 606/32, 27, 41
See application file for complete search history.

(56) References Cited

U.S. PATENT DOCUMENTS

| | | | |
|---|---|---|---|
| 4,936,281 A * | 6/1990 | Stasz | 600/439 |
| 5,295,484 A | 3/1994 | Marcus et al. | |
| 5,596,995 A | 1/1997 | Sherman et al. | |
| 5,658,892 A * | 8/1997 | Flotte et al. | 514/44 |
| 5,788,636 A | 8/1998 | Curley | |
| 5,876,340 A * | 3/1999 | Tu et al. | 600/439 |
| 6,041,253 A * | 3/2000 | Kost et al. | 604/20 |
| 6,235,024 B1 | 5/2001 | Tu | |
| 6,241,725 B1 * | 6/2001 | Cosman | 606/41 |
| 6,326,177 B1 * | 12/2001 | Schoenbach et al. | 435/173.7 |
| 6,495,351 B2 * | 12/2002 | McHale | 435/173.6 |
| 6,607,498 B2 * | 8/2003 | Eshel | 601/2 |
| 6,821,274 B2 * | 11/2004 | McHale et al. | 606/41 |
| 6,835,393 B2 * | 12/2004 | Hoffman et al. | 424/450 |
| 7,037,306 B2 | 5/2006 | Podany et al. | |
| 7,074,218 B2 | 7/2006 | Washington et al. | |
| 7,165,451 B1 * | 1/2007 | Brooks et al. | 73/579 |
| 2005/0043726 A1 | 2/2005 | McHale et al. | |

FOREIGN PATENT DOCUMENTS

| | | |
|---|---|---|
| EP | 0 468 487 | 7/1991 |
| WO | WO 97/18855 | 5/1997 |
| WO | WO 97/40679 | 11/1997 |

* cited by examiner

*Primary Examiner*—Brian L. Casler
*Assistant Examiner*—Jacqueline Cheng
(74) *Attorney, Agent, or Firm*—Frommer Lawrence & Haug LLP; Thomas J. Kowalski; Deborah L. Lu

(57) ABSTRACT

Described and claimed is the combined use of an electric field and ultrasound to ablate a cell or tissue, the use of ultrasound to disrupt a nucleated cell which has previously been electrosensitised by exposure to an electric field, and the use of an electric field for sensitising a nucleated cell to ultrasound. We furthermore disclose the use of electricity to disrupt a nucleated cell which has previously been sensitised by exposure to ultrasound, and the use of ultrasound for sensitising a nucleated cell to electricity.

28 Claims, 15 Drawing Sheets

C T

Positive control ical. However at the focal point the accumulated energy is raised to a pre-determined higher intensity and tissue destruction occurs at or around that focal point. This has the advantage of being relatively selective and prevents major damage to intervening tissues.

ULTRASOUND THERAPY

REFERENCE TO RELATED APPLICATIONS

This application is a continuation-in-part of International Patent Application PCT/GB01/05065 filed Nov. 16, 2001 and published as WO 02/40093 on May 23, 2002, which application claims priority to Great Britain Application Numbers: 0028121.2 filed Nov. 17, 2000; 0105643.1 filed Mar. 7, 2001; and 0120582.2 filed Aug. 23, 2001; and which application also claims priority to U.S. application Ser. Nos. 60/279,812 filed Mar. 29, 2001 and 60/322,388 filed Sep. 14, 2001. This application is also a continuation-in-part of U.S. application Ser. No. 10/113,173 filed Mar. 29, 2002 now U.S. Pat. No. 6,821,274.

Each of the foregoing applications, and each document cited or referenced in each of the foregoing applications, including during the prosecution of each of the foregoing applications ("application cited documents"), and any manufacturer's instructions or catalogues for any products cited or mentioned in each of the foregoing applications and articles and in any of the application cited documents, are hereby incorporated herein by reference. Furthermore, all documents cited in this text, and all documents cited or referenced in documents cited in this text, and any manufacturer's instructions or catalogues for any products cited or mentioned in this text or in any document hereby incorporated into this text, are hereby incorporated herein by reference. Documents incorporated by reference into this text or any teachings therein may be used in the practice of this invention. Documents incorporated by reference into this text are not admitted to be prior art.

FIELD

The present invention relates to the use of a combination of electric field energy and ultrasound energy for the selective ablation of cells or tissues, such as tumour tissues, in an organism.

BACKGROUND

In general therapeutic applications of ultrasound in the clinic may be divided into two major categories; applications that employ low intensity (0.125-3 W/cm$^2$) and those that employ higher intensities ($\geq$5 W/cm$^2$) (ter Haar, (1999) *Eur. J. Ultrasound* 9:3). The former is commonly used in applications such as physiotherapy including the stimulation of normal physiological responses to injury or to accelerate some processes such as transport of drugs across the skin. Treatment with low intensity ultrasound rarely results in collateral tissue damage and indeed extreme efforts are employed to minimise such effects. This includes minimising excessive tissue heating as a result of exposure to the relevant dose of ultrasound. Usually this is accomplished by reducing the treatment time and/or delivering the ultrasound in a pulsed manner.

The major objective of applications involving the use of high intensity ultrasound is to selectively destroy tissue by hyperthermic processes. High intensity ultrasound-mediated tissue ablation may be further categorised on the basis in which the energy is delivered to the tissues. The ultrasound may be delivered directly from the transducer to the treatment area. Alternatively delivery may be mediated by a coupling device which results in focussing of the ultrasound. During the latter the ultrasound passing through intervening tissues is usually at low intensity and therefore relatively non-destructive. However at the focal point the accumulated energy is raised to a pre-determined higher intensity and tissue destruction occurs at or around that focal point. This has the advantage of being relatively selective and prevents major damage to intervening tissues.

In general the use of high intensity focussed ultrasound or HIFU exploits heating at the focal point and a number of methods together with devices for achieving focus and tissue ablation have been suggested (see U.S. Pat. Nos. 4,888,746, 5,895,356, 5,938,608 and International Patent Applications WO 9735518A1 and WO 9922652A1).

In addition to a requirement for relatively sophisticated equipment to achieve focussing of high intensity ultrasound, one major disadvantage associated with the use of HIFU involves the potential for the occurrence of cavitation events which, in turn, leads to the formation of destructive or possibly mutagenic free radicals (Miller et al., (1996) *Ultrasound in Med. & Biol.* 22; 1131). An alternative approach involving a mechanism of sensitising the target tissue to low intensity ultrasound (either focussed or non-focussed) would therefore provide advantage.

It has been found that delivery of short, intense electric pulses to cell populations or tissues (in vivo) results in transient permeabilisation and this has provided the basis for what has become known as electrochemotherapy (Heller et al. *Advanced Drug Delivery Rev.* 35,119;1999). It was originally developed to facilitate passage of chemotherapeutic drugs into cancer cells which had become impermeable to those drugs. It has since been developed to a stage where delivery of electric pulses in vivo is being exploited in areas such as gene therapy in order to mediate introduction of DNA to target areas. Devices designed to facilitate delivery of the pulses in vivo under a variety of conditions (transdermal, laparoscopic, catheter, etc.) currently exist (International patent applications WO 9922809A1, WO 9906101A1 [Gentronics Inc.]; WO 9901157A1, WO 9901157A1, and WO 9901158 [Rhone Poulenc Rorer S. A.].

More recently it has been found that exposure of human erythrocytes to short and intense electric pulses which facilitates transient permeabilisation also results in a dramatic sensitisation to low intensity ultrasound (WO/01/07011).

SUMMARY

The present invention relies partially on the discovery that sensitisation of nucleated cells by application of an electric field ("electrosensitisation") renders the cells susceptible to ablation using low intensity ultrasound and thereby provides a means of eliminating unwanted tissues in the body. The invention also relies on the discovery that exposure of a cell to ultrasound followed by exposure to electric fields also results in cell disruption. Thus, exposure of a nucleated cell to ultrasound and an electric field, applied in any order, results in cell disruption.

According to a first aspect of the present invention, we provide the combined use of an electric field and ultrasound to ablate a cell or tissue.

Preferably, the cell or tissue is sensitised by exposure to the electric field or to the ultrasound, such that the cell or tissue is rendered more susceptible to disruption by exposure to the other of the electric field and ultrasound than a cell or tissue which has not been so sensitised. More preferably, the cell or tissue is exposed to the other of the electric field or ultrasound at a frequency and energy sufficient to cause disruption of the sensitised cell or tissue but insufficient to cause disruption of unsensitised cells or tissues.

In one embodiment, the electric field sensitises the cell or tissue to subsequent exposure to ultrasound.

We provide, according to a third aspect of the present invention, the use of ultrasound to disrupt a nucleated cell which has previously been electrosensitised by exposure to an electric field.

As a fourth aspect of the present invention, there is provided, use of an electric field for sensitising a nucleated cell to ultrasound.

In another embodiment, the ultrasound sensitises the cell or tissue to subsequent exposure to an electric field.

We provide, according to a fifth aspect of the present invention, the use of electricity to disrupt a nucleated cell which has previously been sensitised by exposure to ultrasound.

The present invention, in a sixth aspect, provides use of ultrasound for sensitising a nucleated cell to electricity.

In a seventh aspect of the present invention, there is provided a method for ablating a cell or a tissue, the method comprising the steps of: (a) exposing the cell or tissue to an electric field to render it more susceptible to disruption by ultrasound than a cell or tissue which has not been so exposed; and (b) causing disruption of the exposed cell by applying ultrasound.

According to an eighth aspect of the present invention, we provide a method for ablating a cell or a tissue, the method comprising the steps of: (a) exposing the cell or tissue to an electric field to electrosensitise it; and (b) causing disruption of the electrosensitised cell by applying ultrasound at a frequency and energy sufficient to cause disruption of the electrosensitised cell but insufficient to cause disruption of unsensitised cells.

Preferably, the cell is part of a tissue mass and a proportion of the tissue is sensitised. More preferably, the cell, tissue or tissue mass is comprised in an organism. Most preferably the tissue or tissue mass comprises a tumour tissue.

In a preferred embodiment, the cell disruption or cell or tissue ablation is a result of apoptosis of the cell, tissue or tissue mass.

The cell, tissue or tissue mass may be exposed to an agent which is capable of facilitating cell death. Preferably, the cell death facilitating agent is selected from the group consisting of an oligonucleotide, a ribozyme, an antibody, and enzyme, a cytotoxic agent, a cytostatic agent, a cytokine, GM-CSF, IL-2, an immunogen, a nucleic acid encoding any of the above, a cell producing or expressing any of the above, and combinations thereof.

In a preferred embodiment, the electric field is from about 1 Volt/cm to about 10 kVolts/cm under in vivo conditions. Furthermore, the electric field is preferably applied for between 1 μs and 100 milliseconds. The applied ultrasound is preferably at a power level of from about 0.05 W/cm$^2$ to about 100 W/cm$^2$.

In a highly preferred embodiment, the electric field is applied to the cell, tissue or tissue mass at a field strength of between 10V/cm and 20V/cm. The electric field is applied preferably for a period of 100 milliseconds or more, preferably 15 minutes or more. Preferably, the electric field is applied in continuously, or in a pulsed manner.

The applied ultrasound may be selected from continuous wave ultrasound and pulsed wave ultrasound.

There is provided, in accordance with a ninth aspect of the present invention, a method of inducing apoptosis in a cell, the method comprising exposing the cell to an electric field, and exposing the cell to ultrasound.

As an tenth aspect of the invention, we provide a method of identifying a gene product which is involved in an apoptotic process or in modulating such a process, the method comprising the steps of: (a) inducing apoptosis in a cell by exposing the cell to an electric field and ultrasound; and (b) detecting a gene product which is up-regulated, down-regulated, or otherwise modulated in expression.

We provide, according to a eleventh aspect of the invention, there is provided a method of identifying a gene product which is involved in an apoptotic process or in modulating such a process, the method comprising the steps of: (a) modulating the function of a gene product, or a gene encoding the gene product, in a cell; (b) exposing the cell to an electric field; (c) exposing the cell to ultrasound; and (d) determining whether the gene or gene product modulation has an effect on apoptosis.

According to a twelfth aspect of the present invention, we provide a method of identifying a molecule which is capable of modulating apoptosis of a cell, the method comprising the steps of: (a) contacting a cell with a candidate molecule; (b) exposing the cell to an electric field; (c) exposing the cell to ultrasound; and (d) determining whether apoptosis is modulated as a result of the contacting.

There is provided, according to a thirteenth aspect of the present invention, a gene or gene product identified by a method according to tenth or eleventh aspect of the invention, or a modulator of apoptosis identified by a method according to the twelfth aspect of the invention.

Preferably, the ultrasound is applied to the cell after the electric field.

We provide, according to a fourteenth aspect of the present invention, a nucleated cell which has been exposed to ultrasound or an electric field to render it sensitive to disruption by a stimulus. As a fifteenth aspect of the present invention, there is provided a nucleated cell which is rendered sensitive to disruption by ultrasound, as a result of exposure of the cell to an electric field. We provide, according to a sixteenth aspect of the present invention, a nucleated cell which is rendered sensitive to disruption by electricity, as a result of exposure of the cell to ultrasound.

DETAILED DESCRIPTION

Figure 1:
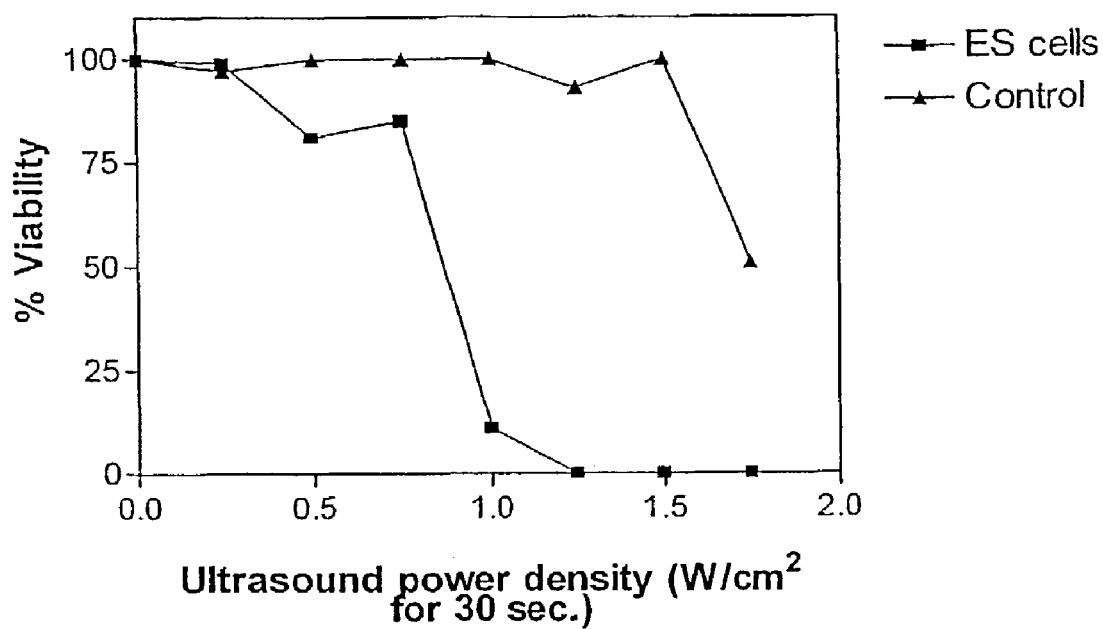
FIG. 1 is a graph of the effect of ultrasound on control ( ) and electro-sensitised ( ) 707 cells in suspension. Cells are electrosensitised by treatment with electric pulses of 3.625 kV/cm at 1:F and cell viability is determined immediately following treatment with ultrasound.

The general mechanism of disruption or ablation of cells comprises two steps: a sensitisation step followed by a disruption step. In general, sensitisation and disruption are achieved by exposure of cells to one or more energy sources, including particles, waves or fields. Preferably, the cells are nucleated cells.

According to the methods and compositions described here, a sensitised nucleated cell is rendered susceptible to disruption by a stimulus. Preferably, a sensitised nucleated cell is rendered more susceptible to disruption by an energy source when compared to a nucleated cell which has not been so sensitised. Disruption is achieved by exposure of a sensitised cell to a stimulus at a frequency and/or energy sufficient to disrupt sensitised nucleated cells, preferably at a frequency and/or energy which is at the same time insufficient to disrupt unsensitised cells.

Thus, a nucleated cell is killed by administration of a sensitiser and a disrupter, in either order. In a preferred embodiment, sensitisation and disruption is achieved by exposure of the cell to ultrasound and electric fields. In the different embodiments disclosed here, the cells are exposed to ultrasound and electricity in either order to achieve sensitisation and disruption. In a preferred embodiment, the methods and compositions described here achieve selective ablation of cells, in other words, targeted cell disruption or killing.

In one aspect, exposure of a cell to an electric field results in sensitivity to disruption by a stimulus, for example, ultrasound energy. Such treatment renders the electrosensitised cell susceptible to ultrasound at a frequency and energy sufficient to cause disruption of the electrosensitised cell but preferably insufficient to cause disruption of unsensitised cells. Preferably, the cell is exposed to an electric field followed by ultrasound.

In another embodiment, exposure of a cell to ultrasound sensitises the cell to disruption by a stimulus, which may include electric energy. Preferably, the cell is exposed to ultrasound followed by an electric field.

In a preferred embodiment, exposure to ultrasound and electric field energy (in either order) results in cell death, cell disruption, cell ablation or cell killing. More preferably such cell death etc results from of apoptosis in the treated cell. Preferably, apoptosis is achieved by administration of electric fields in any combination of (i) high intensity, (ii) short duration, or (iii) as exponential pulses. Most preferably, apoptosis is achieved by administration of electric fields of high intensity, short duration, and as exponential pulses.

In the above passage, the term "high intensity" should be taken to refer to electric fields of between about 0.5 kV/cm and 3 kV/cm, preferably between about 1 kV/cm and 2 kV/cm, more preferably, about 1.3 kV/cm. "Short duration" electric fields in the context of the above passage refer to between about 100 ms to 700 ms, preferably between about 250 ms to 450 ms, more preferably about 250 ms or 450 ms.

We also provide for a cell, preferably a nucleated cell, which has been sensitised by any of the methods described here. Thus, we provide a cell, preferably a nucleated cell, which has been rendered sensitive to a stimulus by exposure to ultrasound or an electric field. Included are cells (preferably nucleated cells) treated with ultrasound, as well as cells (preferably nucleated cells) treated with an electric field, the treatment rendering the cells sensitive to a stimulus. Thus, we provide in particular, nucleated cells which are rendered sensitive to ultrasound by exposure to an electric field, as well as nucleated cells rendered sensitive to an electric field by exposure to ultrasound, by any of the methods and compositions described here.

Preferably, the cell which is ablated is a tumour cell, a cancer cell or a diseased cell, or an otherwise abnormal or unwanted cell Preferably, the cell to be ablated is in a tissue or tissue mass, for example, a growth such as a cyst or a tumour tissue or tumour such as a solid tumour. The tumour may be a benign or a malignant tumour. Thus, the methods described here may be used to treat benign tumours for which traditional tumour therapies (e.g., chemotherapy, radiotherapy, etc) are contraindicated. The methods may also be used as a substitute for any kind of conventional surgery to remove unwanted tissues.

Our methods are applicable to any multicellular organism, and is advantageously applied to organisms having distinct tissues which may be targeted for electrosensitisation. Advantageously, the organism is a mammal. Preferably, the target tissue is a tumour tissue, more preferably a solid tumour tissue. More preferably, the target cell, tissue or tumour etc is treated in situ in the organism.

Preferably, where the tissue is a tumour tissue, treatment of the tissue with the methods described here leads to partial or complete remission. Thus, in a particular embodiment, treatment leads to no significant cell growth of tumour cells (at the treated site or preferably in the body of the organism) within a relevant period. Such a period is preferably 1 day, 1 week, 1 month, 2, 3 4, 5 or 6 months, or even longer, for example, a year, two years, five years, 10 years, 20 years, etc.

Preferably, the sensitisation procedure is carried out in the absence of foreign material, for example, material intended for incorporation into the cell. Thus, for example, where electrosensitisation is followed by application of ultrasound, the electrosensitisation procedure is carried out in the absence of foreign material, for example, material intended for incorporation into the cell.

However, and as described in further detail below, other agents (such as cytotoxics and cytokines), may be applied to the cells after administration of the sensitiser (e.g., electric field) and/or after administration of the disrupter (e.g., ultrasound) to promote cell death. Such cell-death facilitating agents may be administered to prior to the disrupter (e.g., ultrasound), i.e., to sensitised cells. Furthermore, they may be applied together with, or subsequent to, administration of the disrupter, for example, the ultrasound. However, unlike methods for in vivo electroporation of the prior art, the present invention is not primarily concerned with the modification of cell membranes as a result of electrical field energy in order to facilitate the loading of pharmaceuticals or other agents into the cell.

The cell-death facilitating agents may be applied alone or in combination with each other; furthermore, the cell-death facilitating agents may be applied in the form of cells expressing the agents.

Preferably, the cell comprises a nucleated cell. The cell may therefore comprise a nerve cell, a muscle cell, an epidermal cell, a capillary cell, an epithelial cell, an endothelial cell, etc. The cell may be normal, diseased, infected, cancerous, or otherwise abnormal. More preferably, the cell is part of a tissue mass in the organism and a proportion of the tissue is sensitised (e.g., electrosensitised or ultrasound sensitised). The proportion of the tissue which is sensitised will vary, but advantageously, substantially all of the tissue becomes sensitised by electricity or ultrasound. For example, about 50%, 60%, 70%, 80%, 90% or 100% of the cells of the tissue are sensitised by the procedure as described here. More preferably, the cell is a nucleated cell.

Electric field energy is preferably administered substantially as described in the art, using one or more electric pulses of from about 1 Volt/cm to about 10 kVolts/cm under in vivo conditions. Instead of or in addition to the pulses, the electric field may be delivered in a continuous manner. The electric pulse may be applied for between 1 μs and 500 milliseconds, preferably between 1 μs and 100 milliseconds. The electric field may be applied continuously or in a pulsed manner for 5 about minutes.

Ultrasound is advantageously administered at a power level of from about 0.05 W/cm$^2$ to about 100 W/cm$^2$. Diagnostic or therapeutic ultrasound may be used, or combinations thereof.

The sensitisation and disruption may be performed separately or simultaneously. Thus, electrosensitisation and ultrasound disruption, or ultrasound sensitisation and disruption by electric field, may be simultaneous or separate. Where the steps are performed separately, they may be performed in any order. For example, the ultrasound may be administered before the electric field. Advantageously, however, the electrosensitisation step precedes the ultrasound disruption step.

Furthermore, single or multiple applications of electric field, as well as single or multiple applications of ultrasound are also possible, in any order and in any combination. Thus, we envisage the use of multiple cycles of sensitisation, followed by disruption (i.e., S+D, S+D, S+D . . . , for example, ES+US, ES+US, ES+US . . . where ES is electrosensitisation and US is ultrasound). Two or more applications of sensitisation may be followed by a single disruption (i.e., S+S . . . +D). Furthermore, two or more applications of electric field may be followed by a single application of ultrasound (i.e., ES+ES . . . +US), or vice versa (i.e., US+ES+ES . . . ). A single electrosensitising field may be applied, followed by two or more ultrasound applications (e.g., ES+US+US . . . and vice versa (i.e., US+US+ES . . . ). Multiple electrosensitising fields may be applied followed by multiple ultrasound applications (ES+ES . . . +US+US . . . ), or multiple ultrasound applications by multiple electrosensitising fields (US+US . . . +ES+ES . . . ). In each of the above, the ultrasound and/or the electric field may be delivered as single or multiple continuous applications, or as pulses (pulsatile delivery). The above protocols may be combined with each other.

The methods, products etc described here will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning. A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles* and Practice; Oxford University Press; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA* Methods in Enzymology, Academic Press. Each of these general texts is herein incorporated by reference.

Sensitisation

According to a general aspect, cells are sensitised to render them more susceptible to disruption by a stimulus than unsensitised cells. Accordingly, "sensitised" cells are those that have been treated in order to render them more susceptible to disruption by exposure to a stimulus than an unsensitised cell. Such cells are capable of being disrupted at a target site by exposure to a stimulus. Thus, we provide in general a means of disrupting a cell by exposure to sensitiser followed by exposure to a disrupter. Various combinations of sensitisers and disrupters may be employed.

For example, sensitisation may be achieved by exposing the cells to ultrasound. Preferably, such ultrasound sensitised cells are capable of being disrupted by subsequent exposure to an electric field. This aspect is exemplified in Example 11.

However, a preferred means of sensitisation is electrosensitisation. Electrosensitisation is described in our International Patent Application Number PCT/GB00/02848 (published as WO/01/07011), and is described in detail below. The disruption stimuli include laser light and other energy sources, but in a highly preferred embodiment comprises ultrasound.

Electrosensitisation

The term "electrosensitisation" encompasses the destabilisation of cells, such that they are more sensitive to disruption by a stimulus (for example, ultrasound) than otherwise.

According to this method, exposure of a cell to an electric field results in membrane destabilisation and sensitisation of the cell to further stimulus. The cell may be subject to a momentary exposure, or prolonged exposure to electric field. The electric field may be applied in the form of one or more pulses. Alternatively, the cells are exposed to a constantly present field, which may vary in strength, intensity, direction, etc. The strength of the electric field may be adjusted up or down depending upon the resilience or fragility of cells in the targeted tissue.

Electrosensitisation typically occurs in the absence of an agent to be loaded into the cell. Electroporation, which facilitates passage of agents into the cell, occurs in the presence of an exogenous agent to be loaded, and is well known in the art. As noted above, other agents which facilitate cell death may be applied to the cell to promote cell death; however, these agents are typically not present when electrosensitisation takes place.

As used herein, "electric field energy" is the electrical energy to which a cell is exposed during an electrosensitisation procedure as described herein. Preferably the electric field has a strength of from about 1 Volt/cm to about 10 kVolts/cm or more under in vivo conditions (see WO97/49450).

As used herein, the term "electric field" includes one or more pulses at variable capacitance and voltage and including exponential and/or square wave and/or modulated wave and/or modulated square wave forms. References to electric fields and electricity should be taken to include reference the presence of an electric potential difference in the environment of a cell. Such an environment may be set up by way of static electricity, alternating current (AC), direct current (DC), etc, as known in the art. The electric field may be uniform, non-uniform or otherwise, and may vary in strength and/or direction in a time dependent manner.

Electroporation has been used in both in vitro and in vivo procedures to introduce foreign material into living cells. With in vitro applications, a sample of live cells is first mixed with the agent of interest and placed between electrodes such as parallel plates. Then, the electrodes apply an electrical field to the cell/implant mixture. Examples of systems that perform in vitro electroporation include the Electro Cell Manipulator ECM600 product, and the Electro Square Porator T820, both made by the BTX Division of Genetronics, Inc (see U.S. Pat. No 5,869,326).

The known electroporation techniques (both in vitro and in vivo) function by applying a brief high voltage pulse to electrodes positioned around the treatment region. The electric field generated between the electrodes causes the cell membranes to temporarily become porous, whereupon molecules of the agent of interest enter the cells. In known electroporation applications, this electric field comprises a single square wave pulse on the order of 1000 V/cm, of about 100 µs duration. Such a pulse may be generated, for example, in known applications of the Electro Square Porator T820.

Electrosensitisation may be performed in a manner substantially identical to the procedure followed for electroporation, with the exception that the electric field is delivered in the absence of an exogenous agent of interest, as set forth below, and may be carried out at different electric field strengths (and other parameters) from those required for electroporation. For example, lower field strengths may be used for electrosensitisation. Thus, systems for electroporation may be used for delivery of electric fields to cells, tissues, etc, in the methods and compositions described here.

Preferably, the electric field has a strength of from about 1 V/cm to about 10 kV/cm under in vitro conditions. Thus, the electric field may have a strength of 1 V/cm, 2 V/cm, 3 V/cm, 4 V/cm, 5 V/cm, 6 V/cm, 7 V/cm, 8 V/cm, 9 V/cm, 10 V/cm, 20 V/cm, 50 V/cm, 100 V/cm, 200 V/cm, 300 V/cm, 400 V/cm, 500 V/cm, 600 V/cm, 700 V/cm, 800 V/cm, 900 V/cm, 1 kV/cm, 2 kV/cm, 5 kV/cm, 10 kV/cm, 20 kV/cm, 50 kV/cm or more. More preferably from about 0.5 kV/cm to about 4.0 kV/cm under in vitro conditions. Preferably the electric field has a strength of from about 1 V/cm to about 10 kV/cm under in vivo conditions. However, the electric field strengths may be lowered where the number of pulses delivered to the target site are increased. Thus, pulsatile delivery of electric fields at lower field strengths is envisaged.

Preferably the application of the electric field is in the form of multiple pulses such as double pulses of the same strength and capacitance or sequential pulses of varying strength and/or capacitance. As used herein, the term "pulse" includes one or more electric pulses at variable capacitance and voltage and including exponential and/or square wave and/or modulated wave/square wave forms.

Preferably the electric pulse is delivered as a waveform selected from an exponential wave form, a square wave form, a modulated wave form and a modulated square wave form.

A preferred embodiment employs direct current at low voltage. Thus, we disclose the use of an electric field which is applied to the cell, tissue or tissue mass at a field strength of between 1V/cm and 20V/cm, for a period of 100 milliseconds or more, preferably 15 minutes or more.

The use of electric fields for disruption sensitised cells may in general employ the same parameters as those set out above for electricity as a sensitiser.

Ultrasound

According to one aspect, cells which have been sensitised (in particular, electrosensitised) may be disrupted by the application of ultrasound directed at a target tissue and/or cell. According to another aspect, ultrasound may be used as a means of sensitising a cell, i.e., a sensitiser.

As used herein, the term "ultrasound" refers to a form of energy which consists of mechanical vibrations the frequencies of which are so high they are above the range of human hearing. Lower frequency limit of the ultrasonic spectrum may generally be taken as about 20 kHz. Most diagnostic applications of ultrasound employ frequencies in the range 1 and 15 MHz' (From *Ultrasonics in Clinical Diagnosis*, P. N. T. Wells, ed., 2nd. Edition, Publ. Churchill Livingstone [Edinburgh, London & NY, 1977]).

Ultrasound has been used in both diagnostic and therapeutic applications. When used as a diagnostic tool ("diagnostic ultrasound"), ultrasound is typically used in an energy density range of up to about 100 mW/cm$^2$ (FDA recommendation), although energy densities of up to 750 mW/cm$^2$ have been used. In physiotherapy, ultrasound is typically used as an energy source in a range up to about 3 to 4 W/cm$^2$ (WHO recommendation). In other therapeutic applications, higher intensities of ultrasound may be employed, for example, HIFU at 100 W/cm up to 1 kW/cm$^2$ (or even higher) for short periods of time. The term "ultrasound" as used in this specification is intended to encompass diagnostic, therapeutic and focused ultrasound.

Focused ultrasound (FUS) allows thermal energy to be delivered without an invasive probe (see Morocz et al 1998 Journal of Magnetic Resonance Imaging Vol.8, No. 1, pp.136-142. Another form of focused ultrasound is high intensity focused ultrasound (HIFU) which is reviewed by Moussatov et al in Ultrasonics (1998) Vol.36, No.8, pp.893-900 and TranHuuHue et al in Acustica (1997) Vol.83, No.6, pp.1103-1106.

Preferably, a combination of diagnostic ultrasound and a therapeutic ultrasound is employed. This combination is not intended to be limiting, however, and the skilled reader will appreciate that any variety of combinations of ultrasound may be used. Additionally, the energy density, frequency of ultrasound, and period of exposure may be varied. What is important is that the application of ultrasound is able to disrupt the sensitised target cells, or as the case may be, to sensitise them to disruption by application of a stimulus.

Preferably the ultrasound is applied to target tissue with sufficient strength to disrupt sensitised cells but without damaging the surrounding tissues. As used herein, "disrupt" signifies that the target tissue and/or the cells thereof is or are damaged, for example by lysis, necrosis, apoptosis, etc such that the cells are either killed outright or recognised as damaged by the internal defence systems of the organism and eliminated thereby. A tissue or cell is "ablated" when sufficient damage takes place that it is eliminated from the body of the organism.

Preferably the exposure to an ultrasound energy source is at a power density of from about 0.05 to about 100 Wcm$^{-2}$. Even more preferably, the exposure to an ultrasound energy source is at a power density of from about 1 to about 15 Wcm$^{-2}$.

Preferably the exposure to an ultrasound energy source is at a frequency of from about 0.015 to about 10.0 MHz. More preferably the exposure to an ultrasound energy source is at a frequency of from about 0.02 to about 5.0 MHz or about 6.0 MHz. Most preferably, the ultrasound is applied at a frequency of 3 MHz.

Preferably the exposure is for periods of from about 10 milliseconds to about 60 minutes. Preferably the exposure is for periods of from about 1 second to about 5 minutes. More preferably, the ultrasound is applied for about 2 minutes. Depending on the particular target cell to be disrupted, however, the exposure may be for a longer duration, for example, for 15 minutes.

Advantageously, the target tissue is exposed to an ultrasound energy source at an acoustic power density of from about 0.05 Wcm$^{-2}$ to about 10 Wcm$^{-2}$ with a frequency ranging from about 0.015 to about 10 MHz (see WO 98/52609). However, alternatives are also possible, for example, exposure to an ultrasound energy source at an acoustic power density of above 100 Wcm$^{-2}$, but for reduced periods of time, for example, 1000 Wcm$^{-2}$ for periods in the millisecond range or less.

Preferably the application of the ultrasound is in the form of multiple pulses; thus, both continuous wave and pulsed wave (pulsatile delivery of ultrasound) may be employed in any combination. For example, continuous wave ultrasound may be applied, followed by pulsed wave ultrasound, or vice versa. This may be repeated any number of times, in any order and combination. The pulsed wave ultrasound may be applied against a background of continuous wave ultrasound, and any number of pulses may be used in any number of groups.

Preferably, the ultrasound comprises pulsed wave ultrasound. In a highly preferred embodiment, the ultrasound is applied at a power density of 0.7 Wcm$^{-2}$ or 1.25 Wcm$^{-2}$ as a continuous wave. Higher power densities may be employed if pulsed wave ultrasound is used.

Use of ultrasound is advantageous as, like light, it can be focused accurately on a target. Moreover, ultrasound is advantageous as it can be focussed more deeply into tissues unlike light. It is therefore better suited to whole-tissue penetration (such as but not limited to a lobe of the liver) or whole organ (such as but not limited to the entire liver or an entire muscle, such as the heart) therapy. Another important advantage is that ultrasound is a non-invasive stimulus which is used in a wide variety of diagnostic and therapeutic applications. By way of example, ultrasound is well known in medical imaging techniques and, additionally, in orthopaedic therapy. Furthermore, instruments suitable for the application of ultrasound to a subject vertebrate are widely available and their use is well known in the art.

Low Intensity Sensitisation and Disruption

As noted above, low intensity electric fields may be employed to sensitise cells. Low voltage strengths may be set up using alternating current or preferably using direct current (DC). Where direct current is used, it may be applied in either a pulsed or continuous manner, and likewise where alternating current is used. Such cells may preferably be disrupted with low intensity ultrasound.

Thus, in a particular embodiment, direct current at low voltage is used to electrosensitise cells. Electric field strengths as low as from 1V/cm, preferably 5V/cm to 100V/cm more, preferably between 10V/cm and 20V/cm, e.g., 1, 2, 3, 4, 5, 6, 7, 8, 9, 10, 11, 12, 13, 14, 15, 16, 17, 18, 19 or 20V/cm or more may be employed. Electric fields may also be measured in terms of current; preferably, the current applied is between 100 µA to 200 mA, preferably between 1 mA and 10 mA. Thus, the current applied may be about 100 µA, about 200 µA, about 300 µA, about 400 µA, about 500 µA, about 600µA, about 700 µA, about 800 µA, about 900 µA, about 1 mA, about 2 mA, about 3 mA, about 4 mA, about 5 mA, about 6 mA, about 7 mA, about 8 mA, about 9 mA, about 10 mA, about 20 mA, about 50 mA, about 100 mA, about 200 mA, or more.

Where low intensity fields and/or direct current is used, the time of exposure of the cells to the field may typically be in the order of seconds to minutes. Thus, the cells may be exposed to the electric field for more than 100 s, for example, 1 millisecond or more, preferably 0.5 seconds or more. Most preferably, the cells are exposed for more than 1 second, preferably, 5, 10, 30, 60, 120, 180, 240, 300 or more seconds. The cells may be exposed for 1, 2, 3, 4, 5, 6, 7, 8, 9, 10, 15, 20, 25, 30 or more minutes.

The characteristics of the electric field may be constant or vary over the course of exposure, for example, the strength and/or direction of the electric field may be varied. The electric field strength may be steady during the exposure, or may vary in intensity. For example, where the cell is exposed to the field under a constant current setting, the electric field strength may vary. Thus, for example, where a 5 mA constant current is being applied, the electric field strength may vary between 10V/cm and 20V/cm.

In a highly preferred embodiment, the electric field is applied to the cell, tissue or tissue mass at a field strength of between 10V/cm and 20V/cm. The electric field is applied preferably for a period of 100 milliseconds or more, preferably 15 minutes or more. The electric field may be applied continuously or in a pulsed manner.

Treatment of tumours with low voltage/current direct current (DC) without application of ultrasound ("electrochemical treatment") has been described in Nordenstrom, *Am. J. Clin. Oncol.* 1989, 12, 530-536 and Wojcicki et al, *Med. Sci. Monit.* 2000, 6, 498-502. However, in all cases, both in the clinic and in animal models it has been found that such treatment leads to the formation of necrotic lesions and in many cases the target tissues re-establish at the treatment site. The low voltage electrosensitisation described here may however usefully employ the conditions and techniques described in these two documents.

Cells treated with low electric field strengths, for example, using DC, may be disrupted using ultrasound or other stimulus. Such electrosensitised cells may be disrupted by the use of low intensity ultrasound, e.g., in the diagnostic and/or therapeutic ranges: 100 mW/cm$^2$ up to 750 mW/cm$^2$ or in a range up to about 3 to 4 W/cm$^2$ or more, as described in further detail below.

Such treatment with low intensity electric fields, preferably coupled with low intensity ultrasound may be employed for the treatment of benign disorders and also in the cosmetics industry. Benign disorders which may be treated include any disorder which may be cured, treated or addressed by cell or tissue disruption or excision. For example, low intensity ultrasound and/or electric fields may be used to treat skin conditions such as warts, papilomas, psoriasis, eczema, moles, etc. In addition, therapies employing this aspect can be used to accomplish drug- and surgery-free treatment of benign disorders such as benign breast and prostate disease, human papilloma virus (HPV) infection (condylomata acuminata, Longstaff & von Krogh, 2001, Reg. Tox. Pharm. 33, 117-137), eradicating benign granulomatous tissues remaining after localised infections (Hildebrandt et al., 1998, Strahlenther Onkol., 174. 580-588).

Lipomas, which are fatty deposits, as well as other conditions involving deposits of excess fat, may be also treated. Thus, our methods may be used to destroy or disrupt adipose cells or tissue as a substitute for cosmetic treatments such as liposuction.

Furthermore, our methods are suitable for treatment of relatively large areas or parts of the body, particularly for removal of large areas of adipose tissues for cosmetic purposes.

Agents which Facilitate Cell Death

According to a highly preferred embodiment, the target cell, tissue or tissue mass is further exposed to an agent which is capable of facilitating cell death.

An agent which is capable of facilitating cell death is one which, when exposed to a target cell, tissue or tissue mass, is necessary or sufficient to cause cell death. Preferably, such an agent is one which enhances the cell killing ability of treatment with sensitisation and disruption (e.g., electric field/ultrasound administration). Contact with such an agent therefore preferably enhances the cell killing, disruption or ablation effected by sensitisation and disruption, for example, exposure to electric field and ultrasound in any order. In a preferred embodiment, cell-death facilitating agents are used to "mop up" and destroy any cells which have, whether inadvertently or on purpose, been unaffected by the treatment, e.g., application of electric field and ultrasound.

Such facilitating agents may have the ability to promote cell death on their own. Indeed, any agent used for treatment of tumours or cancers as known in the art is a suitable candidate for use as a cell-death facilitating agent. However, the term "agent which facilitates cell death" and "cell death facilitating agent" should be taken to include those agents which work to promote cell death when used in combination with cell sensitisation (for example electrosensitisation) and disruption, for example, ultrasound exposure, as set out above. Preferably, the administration of such cell death facilitating agents enhances cell killing by more than 10%, more than 20%, more than 30%, more than 40%, more than 50%, more than more than 60%, more than 70%, more than 80%, more than 90%, more than 100% compared to the cell killing efficiency of the treatments (e.g., ultrasound/electric field) alone.

The cell-death facilitating agent may work in any number of ways. For example, the agent may be directly toxic to the cell. Agents in this category include cytotoxics, which are used in tumour therapy. The agent may further be one which causes an immune reaction in the host, to the effect that the target cell, tissue, etc is eliminated or killed by the patient's normal immune processes (including both cell-mediated and humoural immune responses). Examples of such agents include cytotoxic T cells and dendritic cells. Furthermore, the agent may comprise an agent which is capable of recruiting immune responses, such as a cytokine. For example, cytokines such as IL-2, GMCSF etc may be used to promote the host's immune response.

The cell-death facilitating agent may be applied directly to the cell, or in its vicinity. It will be appreciated that, where the cell-death facilitating agent is proteinaceous in nature (e.g., a peptide, a polypeptide, a protein, or a fragment of any of these), the cell-death facilitating agent may be administered in the form of a nucleic acid encoding the peptide, polypeptide, etc. Such a nucleic acid may preferably be in the form of an expression vector, and methods for making such vectors and constructs, and the induction of expression from these, are known in the art. Furthermore, we envisage the use of cell-death facilitating agents in the form of cells producing such agents, for example, a cell capable of expressing a cell-death facilitating agent by virtue of comprising a nucleic acid sequence encoding that agent. The cell may be transfected or transformed with a nucleic acid, for example, an expression vector, encoding the cell death facilitating agent, for example, cytotoxic agent, a cytostatic agent, a cytokine, GM-CSF, IL-2 or an immunogen.

The cell-death facilitating agent need not necessarily be molecular in nature. Thus, the use of treatments which cause cell killing by other means, as known in the art, is also encompassed. Examples include the use of radiation, whether applied externally or internally, to kill cells such as tumour cells. Methods of using radiotherapy as primary or auxiliary therapy for tumours is known in the art.

The target cell, tissue or tissue mass may be exposed to the cell-death facilitating agent either before, during or after the stimulus which disrupts the cells, e.g., ultrasound treatment where cells are electrosensitised and then exposed to ultrasound. However, in all cases, the sensitiser (for example, the electric field which electrosensitises the cell, etc) is applied substantially prior to administration of the agent. In other words, the sensitiser is applied to the target in the absence of such a cell death facilitating agent; in particular, where electrosensitisation is employed, the electric field is applied to the target in the absence of a cell death facilitating agent. Thus, the cell death facilitating agent is not primarily responsible for inducing cell disruption or death, but rather acts in a supplementary role to promote cell death of cells, tissues, etc exposed to the sensitiser and disrupter (e.g., electric field and ultrasound).

The cell-death facilitating agent may be exposed to the target cell, tissue or tissue mass by any suitable manner. For example, the agent may be topically applied to the skin; this is advantageous if for example the target cell is epidermal (for example, a skin tumour). Furthermore, the agent may be systemically administered to the patient or to the system of which the target cell, etc forms a part. The agent may be administered orally (taken by mouth), nasally, delivered using liposome technology, etc. The agent may be directly injected into the tumour mass, or at or near the tumour site. The agent may be delivered in the form of a cell expressing the agent, for example a cell expressing a cytotoxic agent. Use of cells expressing such cytotoxic agents, for example, IL-2, is known in the art, and described in for example, Mir et al., *J. Immunotherapy*, 17, 30-38 and Orlowski, et al., 1998, *Anticancer Drugs* 9, 551-556.

The agent may be delivered by being loaded into a suitable carrier, such as a red blood cell carrier. Loading and delivery using red blood cells is disclosed in detail in our International Patent Application numbers PCT/GB00/02848 (published as WO/01/07011) and PCT/GB00/03056. The agent may be delivered into an intracellular compartment by the use of Membrane Translocation Sequences (MTS), as described elsewhere in this document. The agent may also suitably be administered in the form of a pharmaceutical composition, as described in further detail below.

Agents useful in the methods and compositions described here are set out below. Preferred agents which are capable of facilitating cell death include cytokines and cytotoxics, as well as nucleic acids encoding these. These are discussed in further detail elsewhere in this document.

As used herein, the term "agent" includes but is not limited to an atom or molecule, wherein a molecule may be inorganic or organic, a biological effector molecule and/or a nucleic acid encoding an agent such as a biological effector molecule, a protein, a polypeptide, a peptide, a nucleic acid, a peptide nucleic acid (PNA), a virus-like particle, a nucleotide, a deoxyribonucleotide, a ribonucleotide, a synthetic analogue of a nucleotide, a synthetic analogue of a ribonucleotide, a modified nucleotide, a modified ribonucleotide, an amino acid, an amino acid analogue, a modified amino acid, a modified amino acid analogue, a steroid, a proteoglycan, a lipid, a fatty acid and a carbohydrate. An agent may be in solution or in suspension (e.g., in crystalline, colloidal or other particulate form). The agent may be in the form of a monomer, dimer, oligomer, etc, or otherwise in a complex. The agent may be coated with one or more molecules, preferably macromolecules, most preferably polymers such as PEG (polyethylene glycol). Use of a PEGylated agent increases the circulating lifetime of the agent once released.

The cell death facilitating agent may be radioactive, i.e., a radionuclide which is used in radiotherapy. The radionuclide may be a radio-isotope as known in the art, for example cobalt-60, iodine-131, etc, or a molecule such as a nucleic acid, polypeptide, or other molecule as explained below conjugated with such a radio-isotope. As noted above, external radiation sources utilising such radionuclides, in the form of external and/or internal radiotherapy may also be used to facilitate cell death in the treated target cell or tissue.

It will be appreciated that it is not necessary for a single agent to be used, and that it is possible to utilise two or more cell death facilitating agents, sequentially or simultaneously, to achieve cell death. Accordingly, the term "agent" also includes mixtures, fusions, combinations and conjugates, of atoms, molecules etc as disclosed herein. For example, an agent may include but is not limited to: a nucleic acid combined with a polypeptide; two or more polypeptides conjugated to each other; a protein conjugated to a biologically active molecule (which may be a small molecule such as a prodrug); or a combination of a biologically active molecule with an imaging agent.

As used herein, the term "biological effector molecule" or "biologically active molecule" refers to an agent that has activity in a biological system, including, but not limited to, a protein, polypeptide or peptide including, but not limited to, a structural protein, an enzyme, a cytokine (such as an interferon and/or an interleukin) an antibiotic, a polyclonal or monoclonal antibody, or an effective part thereof, such as an Fv fragment, which antibody or part thereof may be natural, synthetic or humanised, a peptide hormone, a receptor, and a signalling molecule. Included within the term "immunoglobulin" are intact immunoglobulins as well as antibody fragments such as Fv, a single chain Fv (scFv), a Fab or a F(ab')$_2$.

Preferred immunoglobulins, antibodies, Fv fragments, etc are those which are capable of binding to antigens in an intracellular environment, known as "intrabodies" or "intracellular antibodies". An "intracellular antibody" or an "intrabody" is an antibody which is capable of binding to its target or cognate antigen within the environment of a cell, or in an environment which mimics an environment within the cell.

Selection methods for directly identifying such "intrabodies" have been proposed, such as an in vivo two-hybrid system for selecting antibodies with binding capability inside mammalian cells. Such methods are described in International Patent Application number PCT/GB00/00876, hereby incorporated by reference. Techniques for producing intracellular antibodies, such as anti-β-galactosidase scFvs, have also been described in Martineau, et al., 1998, *J Mol Biol* 280, 117-127 and Visintin, et al., 1999, *Proc. Natl. Acad. Sci. USA* 96, 11723-11728.

An agent may include a nucleic acid, as defined below, including, but not limited to, an oligonucleotide or modified oligonucleotide, an antisense oligonucleotide or modified antisense oligonucleotide, cDNA, genomic DNA, an artificial or natural chromosome (e.g. a yeast artificial chromosome) or a part thereof, RNA, including mRNA, tRNA, rRNA or a ribozyme, or a peptide nucleic acid (PNA); virus-like particles; a nucleotide or ribonucleotide or synthetic analogue thereof, which may be modified or unmodified; an amino acid or analogue thereof, which may be modified or unmodified; a non-peptide (e.g., steroid) hormone; a proteoglycan; a lipid; or a carbohydrate. If the biological effector molecule is a polypeptide, it may be applied directly to the target area; alternatively, a nucleic acid molecule bearing a sequence encoding the polypeptide, which sequence is operatively linked to transcriptional and translational regulatory elements active in a cell at the target site, may be used. Small molecules, including inorganic and organic chemicals, are also of use. In a particularly preferred embodiment, the biologically active molecule is a pharmaceutically active agent, for example, an isotope.

A preferred embodiment comprises use of a ribozyme or an oligonucleotide such as an antisense oligonucleotide and exposing this to a target cell or tissue to facilitate cell death.

Particularly useful classes of biological effector molecules include, but are not limited to, antibiotics, anti-inflammatory drugs, angiogenic or vasoactive agents, growth factors and cytotoxic agents (e.g., tumour suppressers). Cytotoxic agents of use include, but are not limited to, diptheria toxin, Pseudomonas exotoxin, cholera toxin, pertussis toxin, and the prodrugs peptidyl-p-phenylenediamine-mustard, benzoic acid mustard glutamates, ganciclovir, 6-methoxypurine arabinonucleoside (araM), 5-fluorocytosine, glucose, hypoxanthine, methotrexate-alanine, N-[4-(a-D-galactopyranosyl) benyloxycarbonyl]-daunorubicin, amygdalin, azobenzene mustards, glutamyl p-phenylenediamine mustard, phenolmustard-glucuronide, epirubicin-glucuronide, vinca-cephalosporin,phenylenediamine mustard-cephalosporin, nitrogen-mustard-cephalosporin, phenolmustard phosphate, doxorubicin phosphate, mitomycin phosphate, etoposide phosphate, palytoxin-4-hydroxyphenyl-acetamide, doxorubicin-phenoxyacetamide, melphalan-phenoxyacetamide, cyclophosphamide, ifosfamide or analogues thereof. If a prodrug is applied to the target cell, tissue or tissue mass in inactive form, a second biological effector molecule may be applied. Such a second biological effector molecule is usefully an activating polypeptide which converts the inactive prodrug to active drug form, and which activating polypeptide is selected from the group that includes, but is not limited to, viral thymidine kinase (encoded by Genbank Accession No. J02224), carboxypeptidase A (encoded by Genbank Accession No. M27717), α-galactosidase (encoded by Genbank Accession No. M13571), β-glucuronidase (encoded by Genbank Accession No. M15182), alkaline phosphatase (encoded by Genbank Accession No. J03252 J03512), or cytochrome P-450 (encoded by Genbank Accession No. D00003 N00003), plasmin, carboxypeptidase G2, cytosine deaminase, glucose oxidase, xanthine oxidase, β-glucosidase, azoreductase, t-gutamyl transferase, β-lactamase, or penicillin amidase. Either the polypeptide or the gene encoding it may be administered; if the latter, both the prodrug and the activating polypeptide may be encoded by genes on the same recombinant nucleic acid construct.

Preferably the biological effector molecule is selected from the group consisting of a protein, a polypeptide, a peptide, a nucleic acid, a virus-like particle, a nucleotide, a ribonucleotide, a synthetic analogue of a nucleotide, a synthetic analogue of a ribonucleotide, a modified nucleotide, a modified ribonucleotide, an amino acid, an amino acid analogue, a modified amino acid, a modified amino acid analogue, a steroid, a proteoglycan, a lipid and a carbohydrate or a combination thereof (e.g., chromosomal material comprising both protein and DNA components or a pair or set of effectors, wherein one or more convert another to active form, for example catalytically).

The biological effector molecule is preferably an immunomodulatory agent or other biological response modifier. Also included are polynucleotides which encode metabolic enzymes and proteins, including antiangiogenesis compounds, e.g., Factor VIII or Factor IX.

Cytotoxics

A highly preferred embodiment encompasses the use of one or more agents which facilitate cell death, whether alone or in combination with each other, together with ultrasound/electric field treatment as described. Preferred agents include cytotoxics and cytokines.

"Cytotoxicity" refers to the cell killing property of a chemical compound (such as a food, cosmetic, or pharmaceutical) or a mediator cell (cytotoxic T cell). In contrast to necrosis and apoptosis, the term cytotoxicity need not necessarily indicate a specific cellular death mechanism. For example, cell mediated cytotoxicity (that is, cell death mediated by either cytotoxic T lymphocytes [CTL] or natural killer [NK] cells) combines some aspects of both necrosis and apoptosis. The terms "cytotoxic" and "cytoxic drug" are used interchangeably, and refer to any of a group of drugs that are toxic to cells and cause cell death or prevent any cell process such as cell growth, proliferation, or replication. The latter are also referred to as "cytostats" or "cytostatic drugs".

Preferably, the cytotoxic comprises chemotherapeutic agents having an antitumor effect. Cytotoxics are used mainly to treat cancer, although some have other uses (such as for treatment of other disorders, such as psoriasis and rheumatoid arthritis). Cancer treatment with cytotoxics is known as chemotherapy and has a variety of purposes. The cytotoxics may be used to shrink a tumour before surgery (neoadjuvant chemotherapy); they may be used after the primary tumour has been treated with surgery or radiotherapy to prevent the spread and growth of secondary tumours (adjuvant chemotherapy), or they may be the main treatment for the disease. Chemotherapy may be given to cure the disease or, if cure is not possible, to control its symptoms (palliative chemotherapy).

Cytotoxics suitable for use for preferred embodiments include alkylating drugs, antimetabolites, vinca alkaloids, cytotoxic antibiotics, platinum compounds (e.g. carboplatin), taxanes, topoisomerase inhibitors, procarbazine, crisantaspase, hydroxyurea, Rituximab (a monoclonal antibody) and aldesleukin (an interleukin). Other preferred examples of cytotoxics include bleomycin, neocarcinostatin, suramin, doxorubicin, carboplatin, taxol, mitomycin C, cisplatin, Azathioprine, (Imuran), Cyclophosphamide, (Cytoxan), Methotrexate (Rheumatrex), as well as other cytotoxic drugs related to cyclophosphamide (Cytoxan) including chlorambucil (Leukeran) and nitrogen mustard (Mustargen).

Sex hormones have been used to treat cancer, and may also be used. Tumours of the prostate gland are often stimulated by male sex hormones (the androgens) and so these cancers may be treated with oestrogens (to oppose the androgens) or with anti-androgens. Analogues of gonadorelin, such as buserelin, goserelin, leuprorelin, and triptorelin, may also be used. Some breast cancers are stimulated by oestrogens; such cancers respond to the oestrogen antagonists tamoxifen and toremifene or to aromatase inhibitors. Any of the above cytotoxics may be employed in the preferred methods described here.

Also included within the term "cytotoxic" are cells such as Cytotoxic T lymphocytes (CTL) and Natural Killer (NK) cells. Furthermore, it has been found that compounds which inhibit the effects of VEGF, such as PTK787/ZK 222584, have the potential to provide effective and well-tolerated therapies for the treatment of solid tumours (Wood J M, 2000, *Medicina (B Aires)* 60 Suppl 2:41-7). Accordingly, the use of such compounds as cell-death facilitating agents is also envisaged.

The cytotoxic may be taken by mouth or given by injection or infusion. In general, cytotoxics may be administered in any suitable manner. Preferred routes of administration include administration systemically, orally and nasally. A highly preferred route is local administration to the target tissue. Any suitable formulation, as disclosed in further detail below, may be employed. A combination of two, three, or more cytotoxics, optionally together with one, two, three or more cytokines (as disclosed in further detail elsewhere) may be given. The effects of cytotoxics may need to be carefully monitored and blood tests carried out regularly.

Cytokines

In a further embodiment, the cell-death facilitating agent comprises an agent which is capable of stimulating, reinforcing, recruiting, or boosting an immune response of the patient. Preferably such an immune response is directed against a cell in the target site, preferably, a sensitised cell. More preferably, the cell is an electrosensitised cell which has been exposed to ultrasound, or a ultrasound sensitised cell which has been exposed to an electric field. Most preferably, the cell is a disrupted or ablated cell which has been so exposed. In a highly preferred embodiment, administration of a cell-death facilitating agent results in a cell being destroyed by means of one or more components of the patient's immune system.

Such agents preferably stimulate host immune responses such as recruitment of killer cells such as cytotoxic T-cells and dendritic cells to the target site. For example, immunogens or antigens may be administered to the patient as part of the therapy described here, to enhance cell killing.

The term "cytokine" may be used to refer to any of a number of soluble molecules (e.g., glycoproteins) released by cells of the immune system, which act nonenzymatically through specific receptors to regulate immune responses. Cytokines resemble hormones in that they act at low concentrations bound with high affinity to a specific receptor. Preferably, the term "cytokine" refers to a diverse group of soluble proteins and peptides which act as humoral regulators at nano- to picomolar concentrations and which, either under normal or pathological conditions, modulate the functional activities of individual cells and tissues.

Particular examples of cytokines which are suitable for use in the methods and compositions described include interleukins, lymphokine, interferon, Colony Stimulating Factors (CSFs) such as Granulocyte-Colony Stimulating Factor (G-CSF), Macrophage-Colony stimulating factor (M-CSF) and Granulocyte-Macrophage-Colony stimulating factor (GM-CSF), GSF, Platelet-Activating Factors (PAF), Tumor Necrosis Factor (TNF).

Thus, interleukins such as IL1, IL2 and IL4, as well as interferons such as IFN-$\alpha$, IFN-$\beta$ and IFN-$\gamma$ may be used in the methods described here. Tumour necrosis factors TNF-$\alpha$ (cachetin), TNF-$\beta$ (lymphotoxin) may also be suitably employed.

Preferred cytokines are those which are capable of recruiting immune responses, for example, stimulation of dendritic cell or cytotoxic T cell activity, or which are capable of recruiting macrophages to the target site. In a highly preferred embodiment, the cytokine comprises IL-2, GM-CSF or GSF.

Apoptosis

Cell death can occur by either of two distinct mechanisms, necrosis or apoptosis. In addition, certain chemical compounds and cells are said to be cytotoxic to the cell, that is, to cause its death. According to a preferred aspect, exposure of cells to a sensitiser and a disrupter (e.g., electric field and ultrasound in any order) results in at least a proportion of cells undergoing cell death by apoptosis. Preferably, at least 20% of cell death as a result of treatment by the methods described here is apoptotic. More preferably, at least 40%, 60%, 80% or more, most preferably greater than 95% of cell which die are apoptotic when treated for example with electric field and ultrasound.

The field strengths, time of application, and mode of application of the electric field and/or the ultrasound may be manipulated or adjusted to achieve the desired proportion of cells which undergo death by apoptosis. Apoptosis may be assayed as described below. Thus, a high intensity, short duration exponential electric pulse may be employed, for example, for apoptosis.

The term "high intensity" should be taken to refer to electric fields of between about 0.5 kV/cm and 3 kV/cm, preferably between about 1 kV/cm and 2 kV/cm, more preferably, about 1.3 kV/cm. "Short duration" electric fields in the context of the above passage refer to between about 100 ms to 700 ms, preferably between about 250 ms to 450 ms, more preferably about 250 ms or 450 ms. For example, we disclose the use of a single or multiple electric pulse at 1.33 kV/cm, applied for between about 250 ms to 450 ms, in an exponential fashion, to achieve cell disruption by apoptosis.

"Necrosis" (also referred to as "accidental" cell death) refers to the pathological process which occurs when cells are exposed to a serious physical or chemical insult. Necrosis occurs when cells are exposed to extreme variance from physiological conditions (e.g., hypothermia, hypoxia) which may result in damage to the plasma membrane. Under physiological conditions direct damage to the plasma membrane is evoked by agents like complement and lytic viruses. Necrosis begins with an impairment of the cell's ability to maintain homeostasis, leading to an influx of water and extracellular ions. Intracellular organelles, most notably the mitochondria, and the entire cell swell and rupture (cell lysis). Due to the ultimate breakdown of the plasma membrane, the cytoplasmic contents including lysosomal enzymes are released into the extracellular fluid. Therefore, in vivo, necrotic cell death is often associated with extensive tissue damage resulting in an intense inflammatory response.

"Apoptosis" ("normal" or "programmed" cell death) refers to the physiological process by which unwanted or useless cells are eliminated during development and other normal biological processes. Apoptosis is a mode of cell death that occurs under normal physiological conditions and the cell is an active participant in its own demise ("cellular suicide"). It is most often found during normal cell turnover and tissue homeostasis, embryogenesis, induction and maintenance of immune tolerance, development of the nervous system and endocrine dependent tissue atrophy. Cells undergoing apoptosis show characteristic morphological and biochemical features. These features include chromatin aggregation, nuclear and cytoplasmic condensation, partition of cytoplasm and nucleus into membrane bound vesicles (apoptotic bodies) which contain ribosomes, morphologically intact mitochondria and nuclear material. In vivo, these apoptotic bodies are rapidly recognised and phagocytized by either macrophages or adjacent epithelial cells. Due to this efficient mechanism for the removal of apoptotic cells in vivo no inflammatory response is elicited. In vitro, the apoptotic bodies as well as the remaining cell fragments ultimately swell and finally lyse. This terminal phase of in vitro cell death has been termed "secondary necrosis".

Table 1 summarises the various observable differences between necrosis and apoptosis. Any of these differences, alone or in combination, may be assayed in order to determine whether cell death is occurring by apoptosis or by necrosis.

TABLE 1

Differential features and significance of necrosis and apoptosis.

| | Necrosis | Apoptosis |
|---|---|---|
| Morphological features | Loss of membrane integrity<br>Begins with swelling of cytoplasm and mitochondria<br>Ends with total cell lysis<br>No vesicle formation, complete lysis<br>Disintegration (swelling) of organelles | Membrane blebbing, but no loss of integrity<br>Aggregation of chromatin at the nuclear membrane<br>Begins with shrinking of cytoplasm and condensation of nucleus<br>Ends with fragmentation of cell into smaller bodies<br>Formation of membrane bound vesicles (apoptotic bodies)<br>Mitochondria become leaky due to pore formation involving proteins of the bcl-2 family. |
| Biochemical features | Loss of regulation of ion homeostasis<br>No energy requirement (passive process, also occurs at 4° C.)<br>Random digestion of DNA (smear of DNA after agarose gel electrophoresis)<br>Postlytic DNA fragmentation (= late event of death) | Tightly regulated process involving activation and enzymatic steps<br>Energy (ATP)-dependent (active process, does not occur at 4° C.)<br>Non-random mono- and oligonucleosomal length fragmentation of DNA (Ladder pattern after agarose gel electrophoresis)<br>Prelytic DNA fragmentation Release of various factors (cytochrome C, AIF) into cytoplasm by mitochondria<br>Activation of caspase cascade<br>Alterations in membrane asymmetry (i.e., translocation of phosphatidyl-serine from the cytoplasmic to the extracellular side of the membrane) |
| Physiological significance | Affects groups of contiguous cells<br>Evoked by non-physiological disturbances (complement attack, lytic viruses, hypothermia, hypoxia, ischemica, metabolic poisons)<br>Phagocytosis by macrophages<br>Significant inflammatory response | Affects individual cells<br>Induced by physiological stimuli (lack of growth factors, changes in hormonal environment)<br>Phagocytosis by adjacent cells or macrophages<br>No inflammatory response |

Reference is made to the following documents, which describe apoptosis in detail, as well as various assays for measuring cell death by apoptosis: Schwartzman, R. A. and Cidlowski, J. A. (1993). *Endocrine Rev.* 14, 133; Vermes, I. and Haanan, C. (1994). *Adv. Clin. Chem.* 31, 177; Berke, G. (1991). *Immunol. Today* 12, 396; Krähenbühl, O. and Tschopp, J. (1991). *Immunol. Today* 12, 399; Van Furth, R. and Van Zwet, T. L. (1988). *J. Immunol; Methods* 108, 45. Cohen, J. J. (1993) *Apoptosis. Immunol. Today* 14, 126; Savill, J. S. et al. (1989). *J. Clin. Invest.* 83, 865; Wyllie, A. H. (1980). *Nature* 284, 555; Leist, M. et al. (1994) *Biochemica No.* 3, 18-20; Fraser, A. and Evan, G. (1996) Cell 85, 781-784; Duke, R. C. (1983). *Proc. Natl. Acad. Sci. USA* 80,6361; Duke, R. C. & Cohen, J. J. (1986). *Lymphokine Res.* 5, 289; Trauth, B. C. et al. (1994) *Eur. J. Cell. Biol.* 63, 32,Suppl 40; Matzinger, P. (1991). *J. Immunol; Methods* 145, 185; Kaeck, M. R. (1993); *Anal. Biochem.* 208, 393; Prigent, P. et al. (1993). *J. Immunol; Methods* 160, 139; Huang, P. & Plunkett, W. (1992); *Anal. Biochem.* 207, 163; Bortner, C. D. et al. (1995) *Trends Cell Biol.* 5, 21; Gold, R. et al. (1994); *Lab. Invest.* 71, 219.

Apoptosis and cell mediated cytotoxicity are characterised by cleavage of the genomic DNA into discrete fragments prior to membrane disintegration. Accordingly, apoptosis may be assayed by measuring DNA fragmentation, for example, by observing the presence of DNA ladders. DNA fragments may be assayed, for example, as "ladders" (with the 180 bp multiples as "rungs" of the ladder) derived from populations of cells, or by quantification of histone complexed DNA fragments via, for example, ELISA. Such an assay relies on an one-step sandwich immunoassay to detect nucleosomes. The procedure involves pelleting cells by centrifugation and discarding the supernatant (which contains DNA from necrotic cells that leaked through the membrane during incubation). Cells are resuspended and incubated in lysis buffer. After lysis, intact nuclei are pelleted by centrifugation. An aliquot of the supernatant is transferred to a streptavidin-coated well of a microtiter plate, and nucleosomes in the supernatant are bound with two monoclonal antibodies, anti-histone (biotin-labelled) and anti-DNA (peroxidase-conjugated). Antibody-nucleosome complexes are bound to the microtiter plate by the streptavidin. The immobilised antibody-histone complexes are washed three times to remove cell components that are not immuno-reactive, and the sample is incubated with peroxidase substrate (ABTS®). The amount of coloured product (and thus, of immobilized anti-body-histone complexes) is then determined spectrophotometrically.

Several proteases are involved in the early stages of apoptosis. Apoptosis may therefore also be assayed by detecting the presence of, in addition to, or instead of, assaying the activity of, apoptosis-induced proteases such as caspases, e.g., caspase 3. Caspase activation can be analyzed in different ways, for example, by an in vitro enzyme assay of, for example, cellular lysates by capturing of the caspase and measuring proteolytic cleavage of a suitable substrate. Furthermore, caspases may be assayed by detection of cleavage of an in vivo caspase substrate such as PARP (Poly-ADP-Ribose-Polymer-ase). Cleaved fragments of PARP may be detected with a suitable antibody such as an anti PARP antibody. Protease assays and DNA fragmentation assays are especially suitable for assaying apoptosis in cell populations.

Methods for studying apoptosis in individual cells are also available, such as ISNT and TUNEL enzymatic labeling assays. As noted above, extensive DNA degradation is a characteristic event which often occurs in the early stages of apoptosis. Cleavage of the DNA yields double-stranded, low molecular weight DNA fragments (mono- and oligonucleosomes) as well as single strand breaks ("nicks") in high molecular weight-DNA. In TUNEL, such DNA strand breaks are detected by enzymatic labeling of the free 3'-OH termini with suitable modified nucleotides (such as X-dUTP, X=biotin, DIG or fluorescein). Suitable labeling enzymes include DNA polymerase (nick translation) in ISNT ("in situ nick translation") and terminal deoxynucleotidyl transferase (end labeling) in TUNEL ("TdT-mediated X-dUTP nick end labeling"; Huang, P. & Plunkett, W., 1992, Anal. Biochem. 207, 163; Bortner, C. D. et al., 1995, Trends Cell Biol. 5, 21).

Apoptosis may also be assayed by measuring membrane alterations, including: loss of terminal sialic acid residues from the side chains of cell surface glycoproteins, exposing new sugar residues; emergence of surface glycoproteins that may serve as receptors for macrophage-secreted adhesive molecules such as thrombospondin; and loss of asymmetry in cell membrane phospholipids, altering both the hydrophobicity and charge of the membrane surface. In particular, the human anticoagulant annexin V is a 35-36 kilodalton, $Ca^{2+}$-dependent phospholipid-binding protein that has a high affinity for phosphatidylserine (PS). In normal viable cells, PS is located on the cytoplasmic surface of the cell membrane. However, in apoptotic cells, PS is translocated from the inner to the outer leaflet of the plasma membrane, thus exposing PS to the external cellular environment. Annexin V may therefore be used to detect phos-phatidylserine asymmetrically exposed on the surface of apoptotic cells (Homburg, C. H. E. et al. 1995, *Blood* 85, 532; Verhoven, B. et al., 1995, *J. Exp. Med.* 182, 1597). Furthermore, DNA stains such as DAPI, ethidium bromide and propidium iodide, etc may be used for differential staining to distinguish viable and non-viable cells. Profiles of DNA content may also be used; thus, permeabilized apoptotic cells leak low molecular weight DNA, and detection of "sub-G 1 peaks", or "A 0" cells (cells with lower DNA staining than that of G 1 cells) may be detected by, for example, flow cytometry. Morphological changes characteristic of apoptosis may also be detected in this manner.

Detection of apoptosis-related proteins such as ced-3, ced-4, ced-9 (Ellis, H. M. and Horvitz, H. R., 1986, Cell 44, 817-829; Yuan, J. Y. and Horvitz, H. R., 1990, Dev. Biol. 138, 33-41; Hentgartner, M. O., Ellis, R. E. and Horvitz, H. R., 1992, Nature 356, 494-499.), Fas(CD95/Apo-1; Enari et al., 1996, Nature 380, 723-726), Bcl-2 (Baffy, G. et al., 1993, J. Biol. Chem. 268, 6511-6519; Miyashita, T. and Reed, J. C., 1993, Blood 81, 151-157; Oltvai, Z. N., Milliman, C. L. and Korsmeyer, S. J., 1993, Cell 74, 609-619), p53 (Yonish-Rouach, E. et al., 1991, Nature 352, 345-347), etc by the use of antibodies may also be used to assay apoptosis.

Pharmaceutical Compositions

While it is possible for the composition comprising the cell-death facilitating agent or agents to be administered alone, it is preferable to formulate the active ingredient as a pharmaceutical formulation. The composition may include the cell-death facilitating agent, a structurally related compound, or an acidic salt thereof The pharmaceutical formulations disclosed comprise an effective amount of cell-death facilitating agent together with one or more pharmaceutically-acceptable carriers. The effective amount will vary depending upon the particular conditions of treatment, cell type, as well as other factors including the age and weight of the patient, the general health of the patient, the severity of the symptoms, and whether the cell-death facilitating agent is being administered alone or in combination with other therapies.

Suitable pharmaceutically acceptable carriers are well known in the art and vary with the desired form and mode of administration of the pharmaceutical formulation. For example, they can include diluents or excipients such as fillers, binders, wetting agents, disintegrators, surface-active agents, lubricants and the like. Typically, the carrier is a solid, a liquid or a vaporizable carrier, or a combination thereof. Each carrier should be "acceptable" in the sense of being compatible with the other ingredients in the formulation and not injurious to the patient. The carrier should be biologically acceptable without eliciting an adverse reaction (e.g. immune response) when administered to the host.

The pharmaceutical compositions of use include those suitable for topical and oral administration, with topical formulations being preferred where the tissue affected is primarily the skin or epidermis (for example, a skin tumour). The topical formulations include those pharmaceutical forms in which the composition is applied externally by direct contact with the skin surface to be treated. A conventional pharmaceutical form for topical application includes a soak, an ointment or water-in-oil emulsion, a cream, a lotion, a paste, a gel, a stick, a spray, an aerosol, a bath oil, a solution and the like. Topical therapy is delivered by various vehicles, the choice of vehicle can be important and generally is related to whether an acute or chronic disease is to be treated. Other formulations for topical application include shampoos, soaps, shake lotions, and the like, particularly those formulated to leave a residue on the underlying skin, such as the scalp (Arndt et al, in Dermatology In General Medicine 2:2838 (1993)).

In general, the concentration of the cell-death facilitating agent in the topical formulation is in an amount of about 0.5 to 50% by weight of the composition, preferably about 1 to 30%, more preferably about 2-20%, and most preferably about 5-10%. The concentration used can be in the upper portion of the range initially, as treatment continues, the concentration can be lowered or the application of the formulation may be less frequent. Topical applications are often applied twice daily. However, once-daily application of a larger dose or more frequent applications of a smaller dose may be effective. The stratum corneum may act as a reservoir and allow gradual penetration of a drug into the viable skin layers over a prolonged period of time. A skin penetration enhancer which is dermatologically acceptable and compatible with the cell-death facilitating agent can be incorporated into the formulation to increase the penetration of the active compound(s) from the skin surface into epidemal keratinocytes. Skin penetration enhancers are well known in the art. For example, dimethyl sulfoxide (U.S. Pat. No. 3,711,602); oleic acid, 1,2-butanediol surfactant (Cooper, J. Pharm. Sci., 73:1153-1156 (1984)); a combination of ethanol and oleic acid or oleyl alcohol (EP 267,617), 2-ethyl-1,3-hexanediol (WO 87/03490); decyl methyl sulphoxide and Azone.RTM. (Hadgraft, Eur. J. Drug. Metab. Pharmacokinet, 21:165-173 (1996)); alcohols, sulphoxides, fatty acids, esters, Azone.RTM., pyrrolidones, urea and polyoles (Kalbitz et al, Pharmazie, 51:619-637 (1996)). Terpenes such as 1,8-cineole, menthone, limonene and nerolidol (Yamane, J. Pharmacy & Pharmocology, 47:978-989 (1995)); Azone.RTM. and Transcutol (Harrison et al, Pharmaceutical Res. 13:542-546 (1996)); and oleic acid, polyethylene glycol and propylene glycol (Singh et al, Pharmazie, 51:741-744 (1996)) are known to improve skin penetration of an active ingredient.

For some applications, it is preferable to administer a long acting form of cell-death facilitating agent using formulations known in the art, such as polymers. The cell-death facilitating agent can be incorporated into a dermal patch (Junginger, H. E., in Acta Pharmaceutica Nordica 4:117 (1992); Thacharodi et al, in Biomaterials 16:145-148 (1995); Niedner R., in Hautarzt 39:761-766 (1988)) or a bandage according to methods known in the arts, to increase the efficiency of delivery of the drug to the areas to be treated. Optionally, the topical formulations can have additional excipients for example; preservatives such as methylparaben, benzyl alcohol, sorbic acid or quaternary ammonium compound; stabilizers such as EDTA, antioxidants such as butylated hydroxytoluene or butylated hydroxanisole, and buffers such as citrate and phosphate.

The pharmaceutical composition can be administered in an oral formulation in the form of tablets, capsules or solutions. In general, the daily oral dose of cell-death facilitating agent is less than 1200 mg, and more than 100 mg. The preferred daily oral dose is about 300-600 mg. Oral formulations are conveniently presented in a unit dosage form and may be prepared by any method known in the art of pharmacy. The composition may be formulated together with a suitable pharmaceutically acceptable carrier into any desired dosage form. Typical unit dosage forms include tablets, pills, powders, solutions, suspensions, emulsions, granules, capsules, suppositories. In general, the formulations are prepared by uniformly and intimately bringing into association the cell-death facilitating agent composition with liquid carriers or finely divided solid carriers or both, and as necessary, shaping the product. The active ingredient can be incorporated into a variety of basic materials in the form of a liquid, powder, tablets or capsules to give an effective amount of active ingredient to treat skin proliferation disease.

Other therapeutic agents suitable for use herein are any compatible drugs that are effective for the intended purpose, or drugs that are complementary to the formulation. As an example, the treatment with a formulation can be combined with other treatments such as a topical treatment with corticosteroids, calcipotrine, coal tar preparations, a systemic treatment with methotrexate, retinoids, cyclosporin A and photochemotherapy. The combined treatment is especially important for treatment of an acute or a severe skin proliferation disease. The formulation utilized in a combination therapy may be administered simultaneously, or sequentially with other treatment, such that a combined effect is achieved.

Assays

The observation that cells exposed to electric fields and ultrasound exhibit cell death through apoptosis may be used as the basis of assays to identify useful molecules and targets for therapy.

One such assay seeks to identify molecules such as compounds which are capable of modulating a process involved in apoptosis of a cell. For example, assays which identify molecules which modulate (i.e., promote or inhibit) caspases or other apoptosis protease activity are envisaged. The assays in general involve contacting a cell with a candidate molecule, i.e., a molecule or compound which is suspected of having apoptosis modulatory activity. Such candidate molecules may be provided in the form of libraries such as combinatorial libraries as known in the art. The cell is then treated by exposure to a sensitiser (e.g., an electric field) followed by a disrupter (e.g., ultrasound) as described above, at levels which are known, or have been determined to be, capable of inducing apoptosis in cells of the particular type or characteristics, etc. The progress or degree of apoptosis is observed to identify molecules which are capable of enhancing, promoting, inhibiting or stopping apoptosis of the cells. Molecules identified by such an assay are useful as drugs to enhance or inhibit apoptotic cell death, and may be used as therapies of diseases in which apoptotic cell death is exhibited.

Another assay is capable of identifying genes which are involved in regulating apoptosis, or genes which are involved in apoptotic processes. Such an assay relies essentially on modulating the function of a gene or gene product which is suspected of being involved in, or involved in regulating, an apoptosis process. By gene product, we mean an RNA transcribed from the gene, or a polypeptide product of the gene. For example, gene function may be disrupted by mutation, as known in the art, or by use of a known inhibitor of a gene product, for example, antisense RNA, or a chemical inhibitor. The cell is then exposed to a sensitiser and a disrupter (e.g., an electric field and ultrasound), at levels which are known, or have been determined to be, capable of inducing apoptosis in cells of the particular type or characteristics, etc, and the presence, degree or rate of apoptosis observed. Similarly, gene function may be enhanced and apoptosis assayed. Candidate genes which are suspected of being involved in apoptosis may then be used as potential targets for drug discovery programs, to identify candidate modulators of apoptosis (for example, by use of the above assay).

The invention is further described, for the purpose of illustration only, in the following examples.

EXAMPLES

Example 1

The Effect of Low Intensity Ultrasound on Cells Treated with Pulses of 3.625 kV/cm The target cell line employed in these studies is a mouse friend leukaemic lymphoblast cell line (clone 707, ECACC no. 91112126 from the European Collection of Animal Cell Cultures) and is maintained in DMEM supplemented with 10% (v/v) foetal bovine serum. Cultures are maintained in a humidified 5% $CO_2$ atmosphere at 37° C. Cells are harvested by centrifugation, washed once in phosphate buffered saline (PBS) and suspended at a concentration of $1.065 \times 10^7$ cells/ml. 0.7 ml aliquots of this suspension are dispensed into electroporation cuvettes (0.4 cm electrode gap) together with 0.1 ml of PBS. Cuvettes are retained on ice and electroporated by delivering two pulses of 3.625 kV/cm at a capacitance of 1 µF. Cells are washed twice in PBS by centrifugation, resuspended in PBS containing $MgCl_2$ (4 mM) (PBS/Mg) and retained at room temperature for 30 min. Cells are washed twice in PBS/Mg containing 10 mM glucose, resuspended in the same buffer and retained at room temperature for 1 hour. A control population of cells is taken through the same procedure except that the electroporation step is omitted. Cell concentrations are adjusted to $1.4 \times 10^7$ cells/ml. 100 µl aliquots of cells are dispensed into microwells from a 96-well plate and positioned on a 3 MHz ultrasound head. Cells are exposed to ultrasound for 30 secs. Viability is determined using trypan blue.

The effect of increasing ultrasound power density on cell viability of normal cells and electrosensitised cells is shown in FIG. 1. The results demonstrate little or no effect on the normal control population of cells up to a power density of 1.5 W/cm$^2$ whereas cell viability decreased to almost 0 at 1 W/cm$^2$ following treatment of the electro-sensitised population. It should be noted that cell viability is determined immediately after exposure to ultrasound. These results demonstrate that it is possible to sensitise the target cells to ultrasound conditions that have no effect on normal cells.

Example 2

The Effect of Low Intensity Ultrasound on Cells Exposed to Pulses of 1.875 and 2.5 kV/cm In order to determine whether or not the pulse electric field strength had any effect on susceptibility of the treated cells to low intensity ultrasound, 0.7 ml aliquots of cells (0.8×10$^7$ cells/ml in PBS/Mg) are dispensed into electroporation cuvettes (0.4 cm electrode gap) together with 0.1 ml of PBS. Cuvettes are retained at room temperature and electroporated as described for Example 1 except that one population is treated with two pulses at 1.875 kV/cm and another is treated with two pulses at 2.5 kV/cm. Cells are transferred to PBS/Mg/glucose and retained at room temperature for 15 min. Samples are treated with ultrasound for 30 sec. and allowed to stand at room temperature for 1 hour prior to determination of cell viability using trypan blue. A control population of cells is taken through the above treatment except that the electroporation event is omitted.

Figure 2:
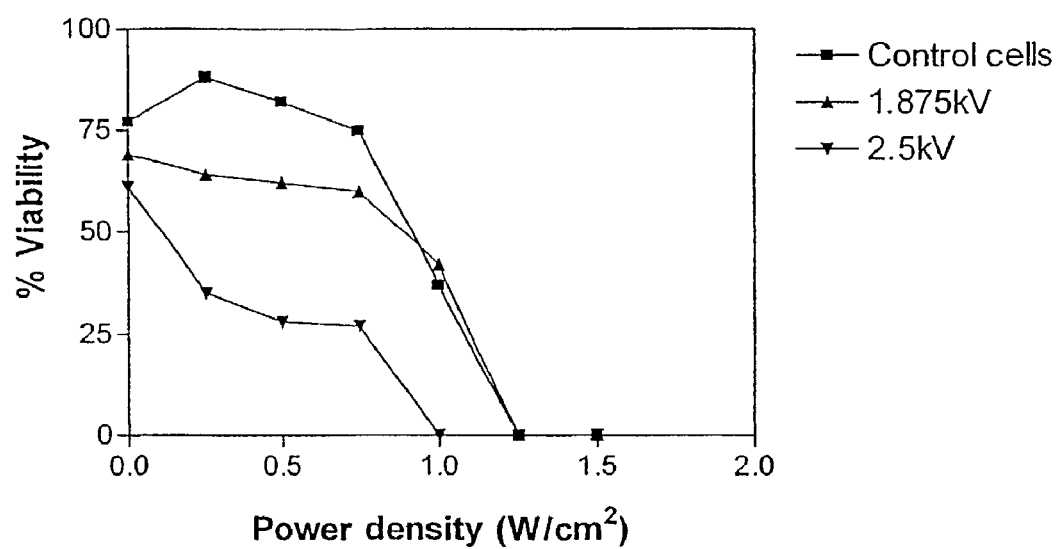
FIG. 2 is a graph of the effect of ultrasound on control cells ( ), cells electro-sensitised at 1.875 kV/cm at 1:F ( ) and cells electro-sensitised at 2.5 kV/cm ( ). Cell viability is determined 1 hour after exposure to ultrasound.

The effect of low intensity ultrasound on cells treated at both voltages is shown in FIG. 2. In this case ultrasound had a limited effect on cell viability in the control population of cells up to 0.75 W/cm$^2$. At or above 1 W/cm$^2$ viability decreased dramatically in the control population. Ultrasound-mediated effects are observed in the population of cells treated with electric pulses of 1.875 kV/cm and viability is decreased at the lower ultrasound densities (0.25-0.75 W/cm$^2$). In the cells treated at 2.5 kV/cm$^2$ stronger effects are noted at all ultrasound power densities examined between 0.25 and 1 W/cm$^2$. The results confirmed that ultrasound sensitivity could be induced by exposure of cell populations to electric pulses. The results also demonstrate that susceptibility of cells to ultrasound increased with increasing electric field strength. The decrease in control cell viability following treatment with ultrasound in this experiment is more dramatic than that observed in Example 1 (FIG. 1) and this may be due to the increased resting time between ultrasound treatment and determination of cell viability described in Example 2.

Example 3

Sensitisation and Ultrasound Treatment of Cells Immobilised in Alginate Matrices In order to determine whether or not this sensitisation phenomenon could be achieved in a mass of cells, thereby mimicking a tumour mass, it was decided to embed the cells in an alginate matrix, expose the mass to electric pulses and subsequently expose it to ultrasound. Viability could then be determined using a modification of the MTT assay described previously (Rollan et al., Bioprocess Eng. 15, 47, 1996). To the above end 707 cells are harvested and suspended in 1% (w/v) sodium alginate (Keltone L V, Lot no. 35245A, Kelco, UK) at a concentration of 1.16×10$^7$ cells/ml. This suspension is added drop-wise to a calcium chloride solution (1.5% [w/v]) and beads (average vol. per bead=10 μl) retained in CaCl$_2$ for 15 min. Beads are subsequently rinsed in PBS and dispensed into electroporation cuvettes (30 beads/cuvette) together with 0.5 ml PBS. Two electric pulses of 2.5 kV/cm at a capacitance of 1 μF are delivered to each cuvette and cells are immediately transferred to culture medium. Aliquots of 5 beads are dispensed into the wells of a 96-well plate and exposed to ultrasound at 0.75 and 1.5 W/cm$^2$ at 3 MHz for 40 seconds. Beads are then placed in an incubator at 37° C. for 165 minutes. Medium is subsequently removed and the beads are washed once in PBS. 1 ml aliquots of MTT (1 mg/ml in PBS) are added to each sample of beads and these are retained at 37° C. for 1 hour. The MTT is then removed from the beads and 0.5 ml of NaOH (1M) is added to each sample. Viability of cells in the beads is determined by measuring the absorbance of the resulting solution at 520 nm using spectophotometry. Control samples consisted of immobilised cells taken through the procedure with the exception of exposure to either electric pulses or ultrasound.

Figure 3:
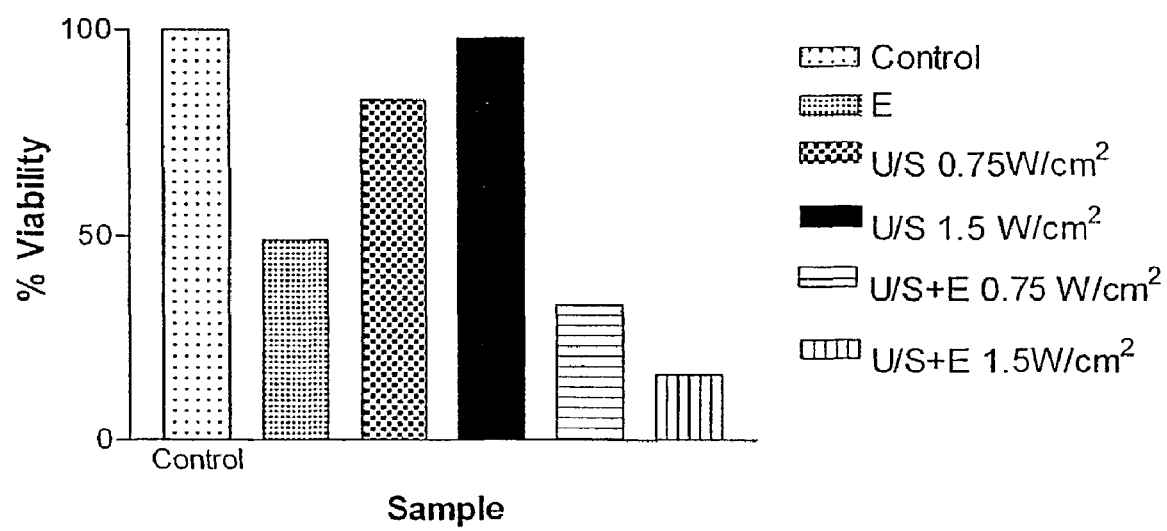
FIG. 3 is a bar chart showing the effect of ultrasound on control and electro-sensitised cells immobilised in calcium alginate matrices.

The results from these experiments are shown in FIG. 3 and they demonstrate that ultrasound exposure at either 0.75 or 1.5 W/cm$^2$ had a very limited effect on control cells which had not been exposed to the electric pulses. Exposure of cells to electric pulses in the absence of ultrasound treatment resulted in a 50% decrease in viability. However, treatment of electrosensitised cells with ultrasound at both power densities had dramatic effects on cell viability where treatment of samples at 1.5 W/cm$^2$ resulted in an 84% reduction in cell viability. It is important to note that the same power density had little or no effect on cell viability in the control sample. The results presented here demonstrate that a mass of cells may be sensitised to ultrasound using electric pulses and suggests that this may also be the case in a tissue mass in vivo.

The above results demonstrate that subjecting cell populations to electric fields in culture render those cells sensitive to low intensity ultrasound.

The following examples demonstrate that when tissue masses are treated with electric fields in vivo, those tissues are sensitive to low intensity ultrasound. These examples make use of a mouse tumour model known as RIF-1 (Twentyman et al., 1980, J. Natl. Cancer Inst., 64 595-604). In Example 4, tumour cells are treated in vitro and these treated populations are then employed to inoculate animals. The development of tumours is monitored. In Example 5, animals are inoculated with the cells and the tumours which develop are treated with electric fields in vivo and subsequently with ultrasound.

Example 4

Tumour Development Following Electrosensitisation and Ultrasound Treatment of Tumour Cells in vitro In this experiment RIF-1 cells are treated with electric fields, ultrasound or a combination of both, and the ability of the treated populations to induce tumour growth is assessed.

The target cells are grown in RPMI 1640 medium supplemented with 10 (v/v) foetal bovine serum and 1% penicillin/streptomycin stock (5000 u/ml and 5000:g/ml, respectively) and in a 5% CO$_2$ humidified atmosphere. Cells are cultured to confluence and then harvested following treatment with trypsin-EDTA (0.005% and 0.002% [w/v], respectively). Cell concentrations are adjusted to 1×10$^6$ cells/ml in phosphate buffered saline and 0.8 ml aliquots are treated with (i) electric fields alone [1 kV/cm, double pulse at 1:F], (ii) ultrasound [1.25 W/cm$^2$ at 3 MHz for 30 sec.] and (iii) electric fields followed immediately by treatment with ultrasound. Control populations consist of cells at the same concentration without treatment. These cell populations are then used to inoculate 8-week old male C3H mice by intradermal injection of 0.1 ml into the rear dorsum of each animal. Tumour volume is calculated from the geometric mean of the diameter measured in 3 dimensions using the formula $4/3\pi r^3$.

Example 4

Results

Figure 4:
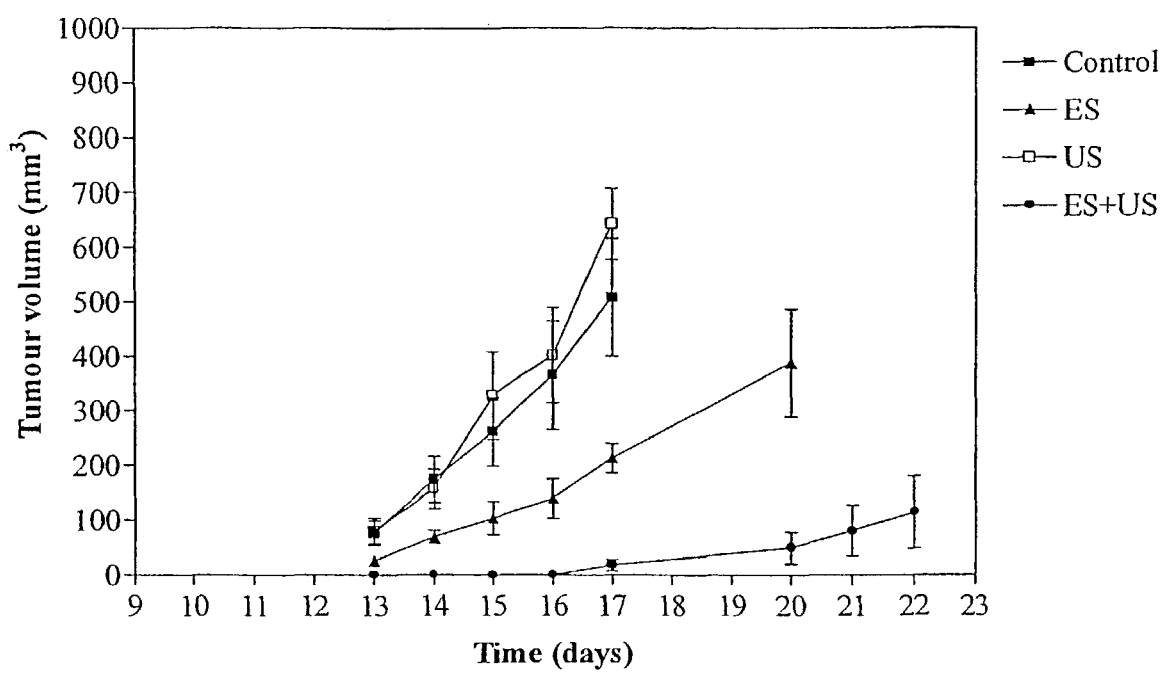
FIG. 4 is a graph testing induction of tumours in C3H mice following treatment of a RIF-1 cell line with electric fields ( ), ultrasound ( ) and electric fields in combination with ultrasound ( ). Control populations ( ) consist of cells which receive no treatment. The x-axis represents time measured in days and the y-axis represents tumour volume measured in mm$^3$.

The results are shown in FIG. 4 and they demonstrate that whilst ultrasound has little or no effect on the ability of the cells to induce tumour growth, electrosensitisation does have a significant effect in this regard. The latter effect has been shown in for example Mir et al., 1991, *Eur J. Cancer*, 27, 68-72.

However, most notably, tumours derived from the cells, which receive the combined electric field and ultrasound, fail to give rise to tumours until day 17. The results demonstrate that the combined treatment has the most dramatic effect on induction of tumour formation and they further suggest a degree of synergy between treatments.

Example 5

Effect of Continuous Wave and Pulse Wave Ultrasound on Electrosensitised Tumour Cells in vivo In this series of experiments tumours are induced in animals and these are employed as targets to determine the effects of in vivo treatments using electric fields, ultrasound (both continuous wave and pulsed) and combined treatments with electric fields followed by ultrasound.

To this end animals are inoculated with RIF-1 tumour cells as described above. When tumours reach an average volume of 50 mm$^3$ they are either untreated (control), treated with electric fields (set voltage=1.66 kV/cm and delivered voltage=1.33 kV/cm using a BTX 630 system together with Tweezertrodes, 7 mm), ultrasound on continuous wave emission at 3 MHz and at 0.7 W/cm$^2$, ultrasound on pulsed wave emission at 3 MHz at 1.8 W/cm$^2$ (duty cycle of 35%) and combinations of the electric field followed immediately by each form of ultrasound. Tumour growth is monitored by measuring tumour volume and this is determined as described above.

Example 5

Results

Figure 5:
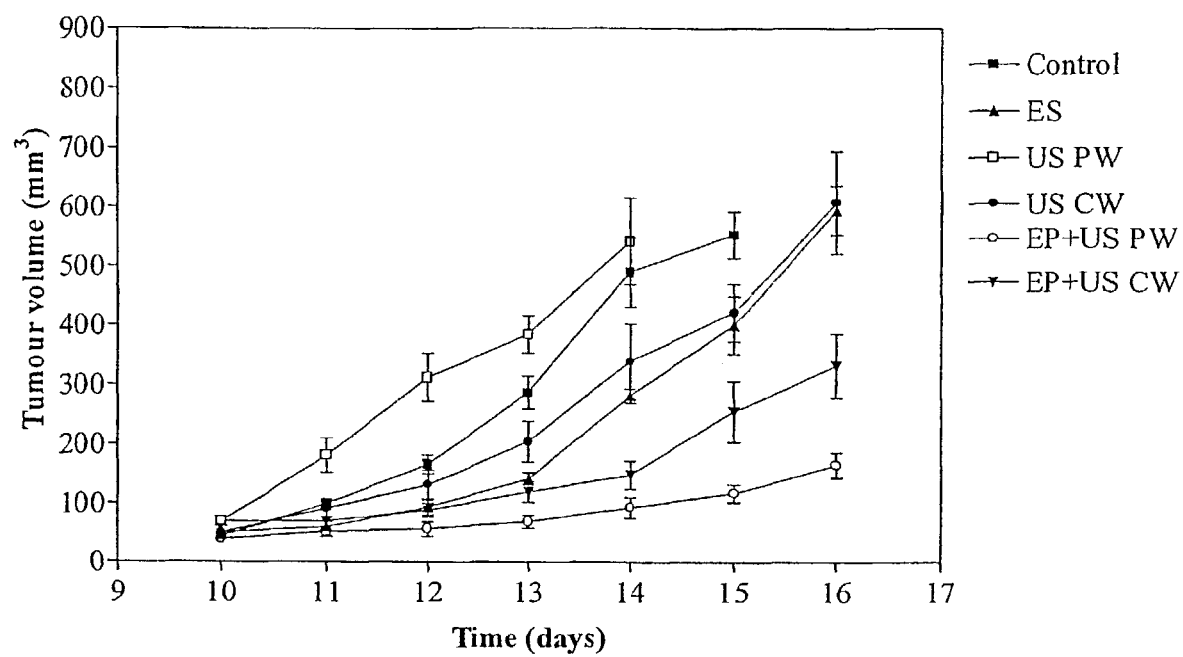
FIG. 5 shows treatment of RIF-1 tumours in situ in mice with electric fields ( ), pulsed wave ultrasound ( ), continuous wave ultrasound ( ), electric field plus continuous wave ultrasound ( ) and electric fields plus pulsed wave ultrasound ( ). Continuous wave ultrasound is delivered at 0.7 W/cm$^2$ at 3 MHz for 2 minutes, while pulsed wave ultrasound is delivered at 1.8 to 1.9 W/cm$^2$ at 3 MHz for 2 minutes at a 35% setting. Electric fields are delivered at 1.333 kV/cm. Control tumours ( ) receive no treatment. The x-axis represents time measured in days and the y-axis represents tumour volume measured in mm$^3$. Error bars represent +/− SEM (standard error mean).

The results are shown in FIG. 5 and they demonstrate that pulsed wave ultrasound treatment alone has no effect on tumour growth. Both electric field treatment alone and continuous wave ultrasound alone appear to have a slight effect on tumour growth. Notably, the combined treatments of electric field and each type of ultrasound show the greatest inhibition of tumour development.

In tumours which are treated with electric fields combined with ultrasound, those treated with pulsed wave ultrasound exhibit the greatest response, although the negative effects on growth following combined treatment with continuous wave ultrasound are also significant. It should be noted, however, that in terms of total energy delivered to the cells, pulsed wave ultrasound appears to be slightly more efficient than continuous wave (78 J/cm$^2$ for pulsed wave ultrasound versus 84 J/cm$^2$ for continuous wave ultrasound).

These results demonstrate that tumours treated with electric pulses in vivo are rendered sensitive to relatively low intensity ultrasound.

Example 6

Sensitisation of Tumour Cells to Ultrasound in vivo Using Square Wave Electric Pulses This Example demonstrates the ability of high intensity and short duration square wave electric pulses to sensitise tumour cells to ultrasound in vivo.

In the above series of experiments is shown that exposing tumours in vivo renders them sensitive to relatively low-intensity ultrasound. In those experiments the manner in which the electric field is delivered to the tissues includes both high-intensity, short duration exponential electric pulses and low intensity direct current for a prolonged period of time.

In order to determine whether or not conditions using short-duration and high intensity square-wave pulses can be employed to facilitate hyper-sensitisation of tumour tissues to ultrasound, tumours are treated with conditions using short-duration and high intensity square-wave pulses and sensitivity to ultrasound determined. To this end a series of tumours are established in animals (n=4 per group) and three groups of animals are treated with 8 square wave pulses consisting of 100: second duration, an electric field strength of 1.25 kV/cm$^2$, delivered at a frequency of 1 Hz. One of these groups is then subjected to treatment immediately with pulsed wave ultrasound (35% continuous wave) for 2 min. at 3.57 W/cm$^2$ and at 1 MHz. Another group receives ultrasound 24 hours after delivery of the electric field and a third group receives no ultrasound. In addition, a control untreated group of animals is employed in the experiment as is a group treated with ultrasound alone. Tumour growth is monitored as described previously.

Example 6

Results

Figure 6:
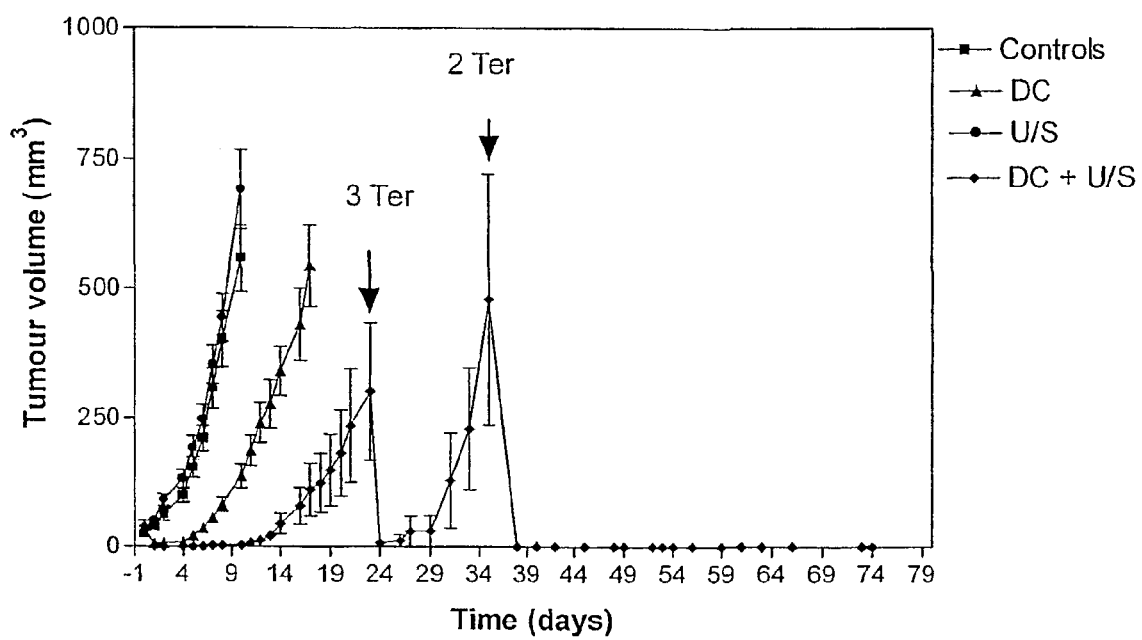
FIG. 6 is a graph showing prolonged monitoring of experiments in which tumours were sensitised with direct current (DC) and subsequently treated with ultrasound. Groups of 6 animals are employed in each group and tumours are treated with ultrasound alone ( ), DC alone ( ) and DC plus ultrasound ( ). Control animals ( ) receive no treatment. The bold arrow insets together with 'Ter' indicates removal of animals from the experiment. Error bars represent +/− SEM (standard error mean).

The results obtained from these experiments are shown in FIG. 6 and they demonstrate that treatment with the electric field alone has a significant effect on tumour growth, as expected (Mir et al.,., Eur J. Cancer, 22, 1991, 68-72). When tumours are treated with the electric fields and immediately thereafter with ultrasound, a significant reduction in tumour growth is observed, although this is not as dramatic as the effect observed using exponential wave or DC treatment. When tumours are treated with ultrasound 24 hours after electric field treatment no significant effect on tumour growth retardation is observed. These results suggest that the electric field conditions short-duration and high intensity square-wave pulses are not as efficient as either exponential wave or DC at sensitising tumours to ultrasound in vivo.

It is however, worth noting that in our studies with high intensity exponential wave treatments the time constants observed during delivery of pulses is in the region of 300-400 msec., whereas the square wave pulses employed here are in the region of 100:sec. In accordance with this, experiments similar to the above, but in which the square wave pulse duration is increased from the :second range to the millisecond range show more dramatic responses in reduction of tumour growth.

Example 7

Effect of Higher Intensity Continuous Wave and Pulse Wave Ultrasound on Electrosensitised Tumour Cells in vivo Animals are inoculated with RIF-1 tumour cells, tumours treated, and tumour growth monitored as described above in Example 5. Treatment comprises electric fields (1.33 kV/cm), ultrasound on continuous wave emission at 3 MHz and at 1.25 W/cm$^2$ for 2 minutes, ultrasound on pulsed wave emission at 3 MHz at 2.5 W/cm$^2$ for 2 minutes (35% continuous wave) and combinations of the electric field followed immediately by each form of ultrasound. Untreated cells are used as control, as above.

Example 7

Results

Figure 7:
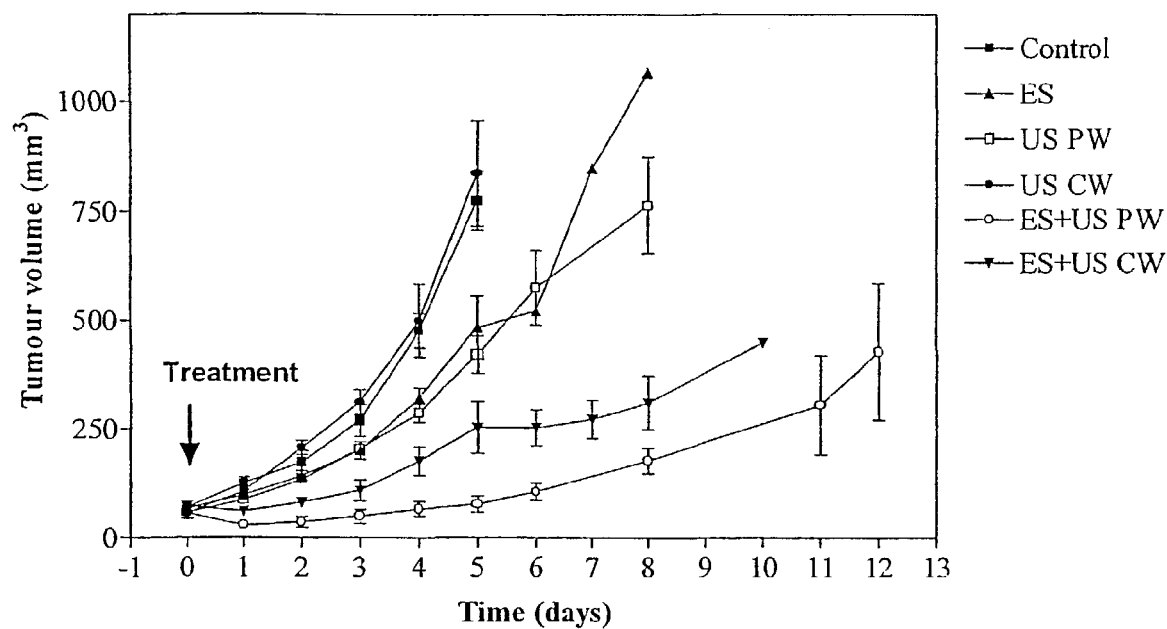
FIG. 7 shows treatment of RIF-1 tumours in situ in mice with electric fields ( ), pulsed wave ultrasound ( ), continuous wave ultrasound ( ), electric field plus continuous wave ultrasound ( ) and electric fields plus pulsed wave ultrasound ( ). Continuous wave ultrasound is delivered at 1.25W/cm$^2$ at 3 MHz for 2 minutes, while pulsed wave ultrasound is delivered at 2.5 W/cm$^2$ at 3 MHz for 2 minutes at a 35% setting. Electric fields are delivered at 1.33 kV/cm. Control tumours ( ) receive no treatment. The x-axis represents time measured in days and the y-axis represents tumour volume measured in mm$^3$. Error bars represent +/− SEM (standard error mean).

The results are shown in FIG. 7 and they demonstrate that both pulsed wave ultrasound treatment and continuous wave treatment of electrosensitised cells are effective in slowing tumour growth. As before, pulsed wave treatment appears to be more effective than continuous wave treatment, even though the total energy delivered to the cells is 105 J/cm$^2$ for pulsed wave ultrasound versus 150 J/cm$^2$ for continuous wave ultrasound.

These results demonstrate that tumours treated with electric pulses in vivo are rendered sensitive to higher intensities of ultrasound.

Example 8

Treatment of Electrosensitised Tumours with Ultrasound At Various Times After the Electrosensitisation Event In the previous Examples ultrasound treatment immediately follows electrosensitisation. In order to examine the length of time tumours remain sensitive to ultrasound after the electrosensitisation event, we decided to electrosensitise tumours in vivo and treat those tumours with ultrasound at various times after electrosensitisation. To this end tumours are inoculated into recipient mice as described above. Those tumours are electrosensitised by exposure to double pulses at 1.33 kV/cm. Tumours are then exposed to ultrasound (3.57 W/cm$^2$, 1 MHz using pulsed wave at 35% continuous wave for 2 min.) at 0, 0.5, 1, 2, 6 and 18 hours after electrosensitisation. Control animals remain untreated or are exposed to either electric field or ultrasound treatment alone. Tumour volume is monitored following treatment as described above.

Example 8

Results

Figure 8:
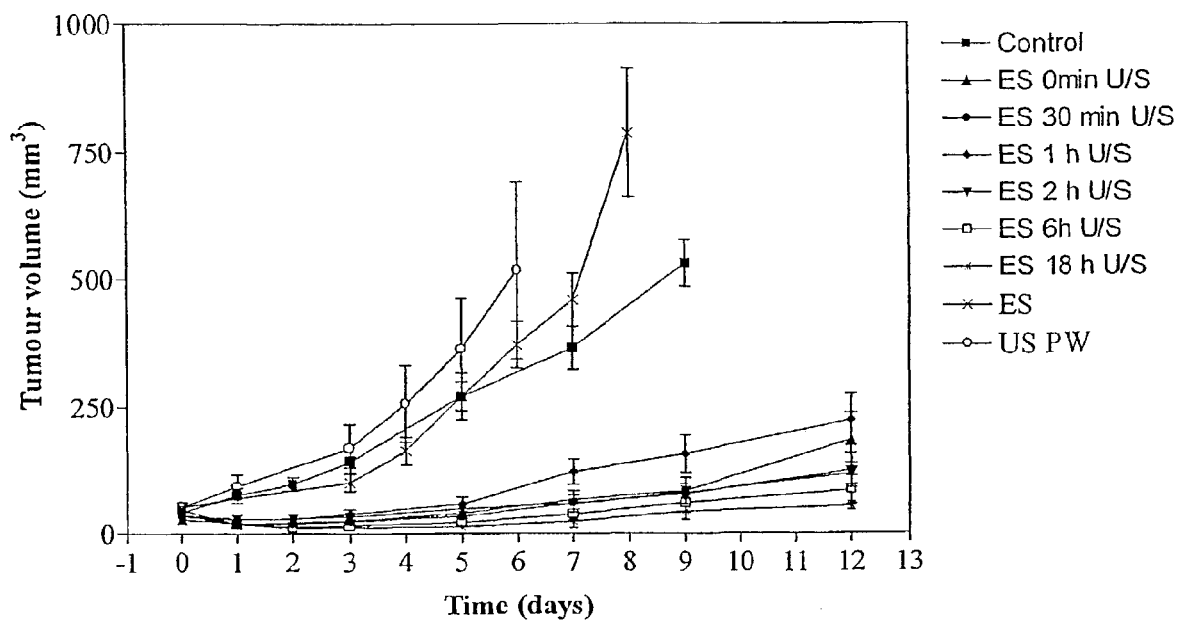
FIG. 8 is a graph showing results of treatment of electrosensitised tumours with ultrasound at 0 ( ), 0.5 ( ), 1 ( ), 2 ( ), 6 ( ) and 18 (τ) hours after electrosensitisation. Control populations consisted of untreated ( ) or treated with electric pulses (ζ) or ultrasound ( ) alone. In these experiments error bars represent ±SEM where n=3.

The results obtained from this experiment are shown in FIG. 8 and they demonstrate that significant effects are detected when ultrasound is delivered at all times post electrosensitisation. These results demonstrate that cells remain electrosensitised to ultrasound for a considerable period of time following electrosensitisation. The results demonstrate that ultrasound does not necessarily have to be delivered immediately after electrosensitisation for cell ablation to take place.

Example 9

Induction of Apoptosis in Cells Treated with Electric Field and Ultrasound

In order to examine the molecular mechanism by which combined exposure of cells to electric fields and ultrasound induces cell death, cells are treated with a single pulse at various voltages and the effects of ultrasound on those cells are examined.

In addition to examining cell numbers remaining following treatment we determine whether or not the remaining population of cells are apoptotic or necrotic. To this end 707 cells are harvested and suspended in PBS at a concentration of 1.53×10$^6$ cells/ml. 0.8 ml aliquots are dispensed into electroporation cuvettes (0.4 cm electrode gap) and cells are treated with single electric pulses at a capacitance of 1:F. Cells are harvested from cuvettes and each 0.8 ml aliquot is washed by centrifugation and resuspended in 2 ml of tissue culture medium containing foetal bovine serum. Each 2 ml aliquot is dispensed into a 2 ml well of a 24-well tissue culture plate. Control populations of cells are not treated with electric pulses but are dispensed into 2 ml wells. All samples are treated with ultrasound for 30 seconds at a power density of 1.25 W/cm$^2$ and using a 3 MHz ultrasound head (single pulse). Cells are then incubated at 37° C. for 21 hours in a humidified 5% CO$_2$ atmosphere. Following incubation, cells are harvested and the proportion of cells which are either apoptotic or necrotic is determined by staining with an Annexin-V-FLOUS staining kit (Roche, UK). Following staining cells are suspended in HEPES buffer and analysed using flow cytometry.

Example 9

Results

Figure 9:
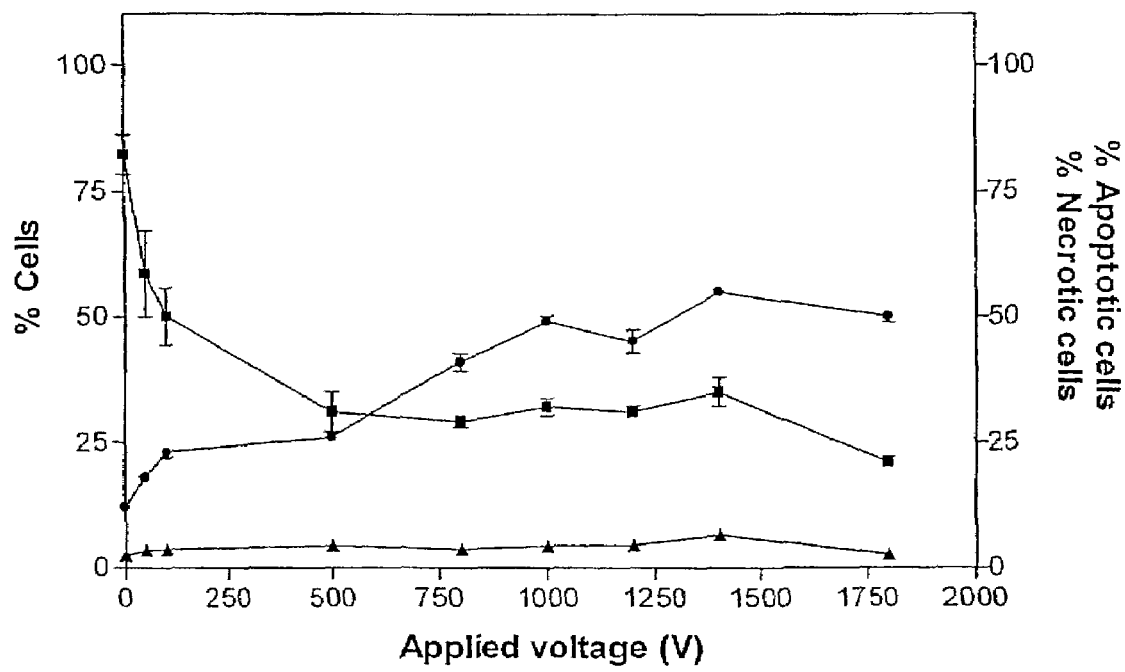
FIG. 9 shows the effect of combined treatment of 707 cells with increasing electric field strength (single pulse) and ultrasound at 1.25 W/cm$^2$ for 30 seconds using a 3 MHz ultrasound head. Cell concentrations ( ) are determined using a haemocytometer and the proportion of apoptotic ( ) and necrotic ( ) cells in each population is determined by staining in Annexin V-FLUOS and propidium iodide followed by analysis using flow cytometry. Data reflect mean values ∀ SEM of three experiments.

The results obtained are shown in FIG. 9. They demonstrate that ultrasound treatment alone results in an approximate 20% decrease in cell numbers. As the voltage is increased, combined treatment leads to a very significant decrease in cell numbers and this finally reaches a steady state above voltages of 750V.

In addition to examining cell numbers in remaining populations, the proportion of both apoptotic and necrotic cells in those surviving populations is examined. The results are also shown in FIG. 9 and they demonstrate that a significantly greater proportion of surviving cells remaining following treatment are apoptotic. These results suggest that treatment of electrosensitised cells with ultrasound facilitates the onset of apoptosis rather than necrosis.

Example 10

Induction of Apoptosis in Tumours Following Treatment with Combined Electric Fields and Ultrasound in vivo As shown in previous Examples, treatment of target cell populations with electric fields and ultrasound leads to the induction of apoptosis in vitro. The objective of this Example is to demonstrate that combined treatment with electric fields followed by treatment with ultrasound in vivo leads to induction of apoptosis.

To the above end RIF-1 tumours are induced in C3H mice and these are employed as target tumours for combined treatments with electric pulses followed by ultrasound. Control animals receive no treatment. Conditions used in electrosensitisation involve treatment with a double pulse regime consisting of 1.33 kV/cm and ultrasound treatment involve the use of pulsed wave ultrasound (35% continuous wave) at 1 MHz, 3.57 W/cm$^2$ for 2 min. Following treatment, tumours from control, untreated animals and those receiving treatment are harvested at 0, 6, 12,18 and 24 hours post treatment. After harvesting tumours are fixed in 4% (w/v) paraformaldehyde overnight. Paraffin wax sections are then prepared for each sample and these are stained using the In situ cell death detection kit, TMR red (Roche, UK) according to the manufacturer's instructions. This staining method is based on terminal deoxynucleotidyl transferase nick end labelling (TUNEL) and apoptosis is indicated by fluorescent staining as observed using fluorescence microscopy.

Example 10

Results

Figure 10:
FIG. 10. Induction of apoptosis in vivo, following treatment with electric fields and ultrasound. Sections from control (Column C) and treated animals (Column T) are stained for apoptosis. Panels from sections harvested at 0, 6, 12, 18 and 24 hours are displayed in descending order in each column. The panel at the bottom of the figure represents a positive control generated by DNAse I treatment of sections prior to staining.
Figure 10:
Figure 10:
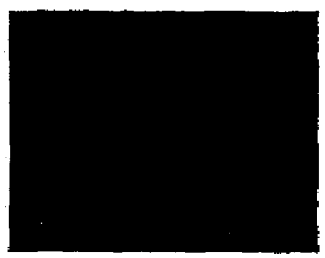
Figure 10:
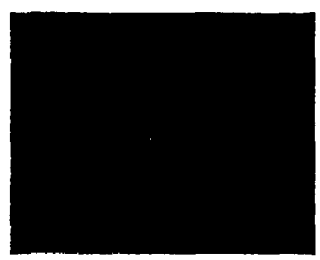
Figure 10:
Figure 10:
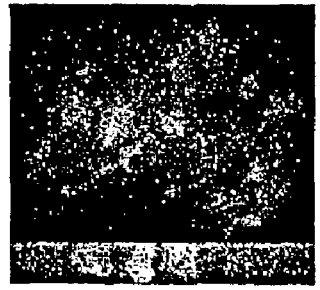
Figure 10:
Figure 10:
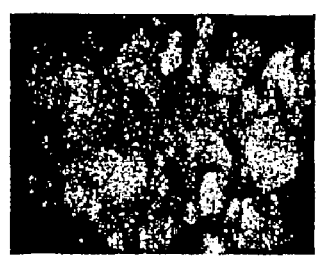
Figure 10:
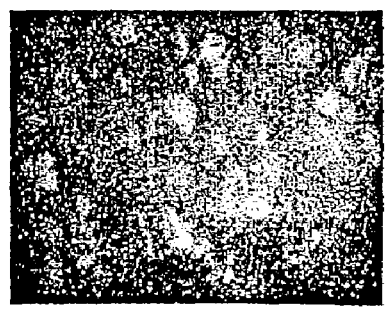

When sections are stained for apoptosis the results obtained following examination with fluorescence microscopy are shown in FIG. 10. In control samples, the only sample that exhibits slight positive staining is the 24 hours sample and this may result from the inclusion of normal cells in the sections. All other control samples fail to yield a signal for apoptosis. In the treated samples, staining for apoptosis becomes strongly evident at 12 hours following treatment and clear signals are also evident at 18 and 24 hours (FIG. 10). The results clearly demonstrate that combined treatment with electric fields and ultrasound results in the onset of apoptosis.

Example 11

Effect of Treating Tumours with Ultrasound Prior to Exposure to Electric Field in vivo In this series of experiments tumours are established in mice as described above for Example 5. However in this Example, the tumours are treated with ultrasound prior to treatment with electric fields.

In this study animals are inoculated with RIF-1 tumours as described above. Tumours are then treated with ultrasound (2 min.) at 1 MHz using a power density of 1.25 W/cm$^2$ at continuous wave and 3.57 W/cm$^2$ at pulsed wave (35% continuous wave) delivery mode. Tumours are then treated immediately with electric fields (double pulse using set voltage=1.66 kV/cm using a BTX 630 system together with Tweezertrodes, 7 mm). Tumour growth is monitored by measuring tumour volume and this is determined as above.

Example 11

Results

Figure 11:
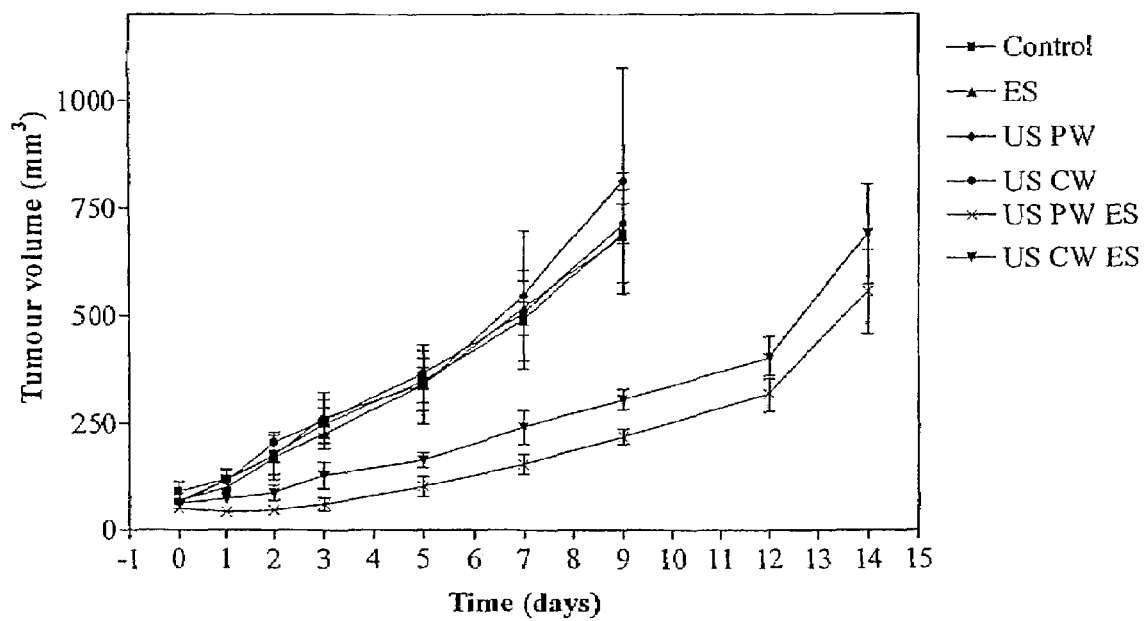
FIG. 11 shows the effect of treating tumours with ultrasound prior to electric fields. Groups of animals used in experiments consist of control untreated ( ), electrosensitised ( ), ultrasound using pulsed wave ( ), ultrasound using continuous wave ( ), pulsed wave ultrasound followed by electric fields (X) and continuous wave ultrasound followed by electric fields ( ). In each group n=4 and the error bars represent + SEM.

The results are shown in FIG. 11 and they demonstrate that treatment of tumours with ultrasound prior to electric fields also has an inhibitory effect on tumour growth. In addition, the inhibitory effect obtained using pulsed wave ultrasound is again greater than that observed using continuous wave ultrasound.

Surprisingly, the results demonstrate that the advantage associated with the use of combined treatment with electric fields and ultrasound in terms of tumour treatment is realised whether ultrasound is delivered prior to or following treatment with electric fields.

Example 12

Effect of Low Voltage Direct Current Electricity Treatment

Relatively intense electric fields are employed in the above examples. However, anti-tumour effects have also been demonstrated following treatment of tumours with low voltage/ direct current (DC) alone (Nordenstrom, *Am. J. Clin. Oncol.* 1989, 12, 530-536; Wojcicki et al., *Med Sci. Monit.* 2000, 6, 498-502). We decided to investigate whether such low voltage/DC can render tumours or other cells hyper-sensitive to relatively low intensity ultrasound.

RIF-1 tumours are established in C3H recipient mice as described above. Needles are then horizontally inserted on each side of the tumours and electrodes attached to the needles. A constant current of 5 mA is established across the needles for a period of 15 min. and are treated immediately with ultrasound at 3.75 W/cm$^2$ for a period of 3 minutes. During the treatment the electric field strength ranges from 10 to 20V/cm, with the field strength increasing as treatment progresses. Control animals are treated with electric current alone. Tumour volume is then monitored as described above.

Example 12

Results

Figure 12:
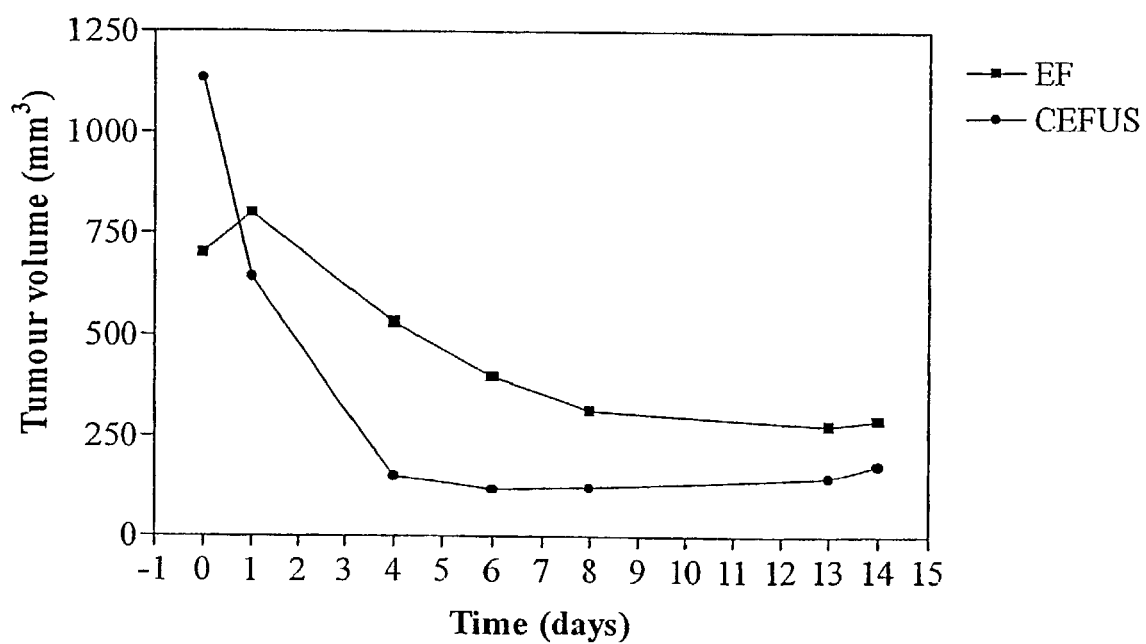
FIG. 12 shows the effect of direct electric current ( ) and direct electric current together with ultrasound ( ) on tumour volume.

The results are shown in FIG. 12 and they demonstrate that in the animal that is treated with electric current alone, the tumour volume decreases significantly over the time period examined. This reaches a minimum at 13 days. This also occurs in the animal that is treated with both electric current and ultrasound. However, the rate at which tumour volume decreases is significantly higher. In this case tumour volume reaches a minimum within 4-6 days.

It should be noted that the starting tumour size in this experiment is much greater than that in other studies described previously and in this context, the decrease in tumour size observed here is very dramatic. These results demonstrate that, although electrosensitisation of tumours to relatively low intensity ultrasound is achieved using pulses of high electric field strength, this phenomenon also occurs using strategies employing low electric field strengths with direct current. This observation broadens the degree of utility of our technology, particularly in cases where large areas of tissue may need to be sensitised.

Example 13

Treatment of Tumours with Direct Current Together with Ultrasound At 5W/Cm$^2$ and 1 Mhz The objective of the experiments in this Example is to examine the effects of ultrasound at increased intensity on direct current-electrosensitised tumours. To this end, RIF-1 tumours are established in recipient C3H mice as described above and treated with (i) direct current alone at 5 mA for 5 min, (ii) pulsed ultrasound alone at 5 W/cm$^2$ for 2 min. at 35% continuous wave, and (iii) direct current plus pulsed ultrasound using the conditions listed above. Tumour volume is measured as described previously. In addition the growth of control, untreated tumours is also monitored.

Example 13

Results

Figure 13:
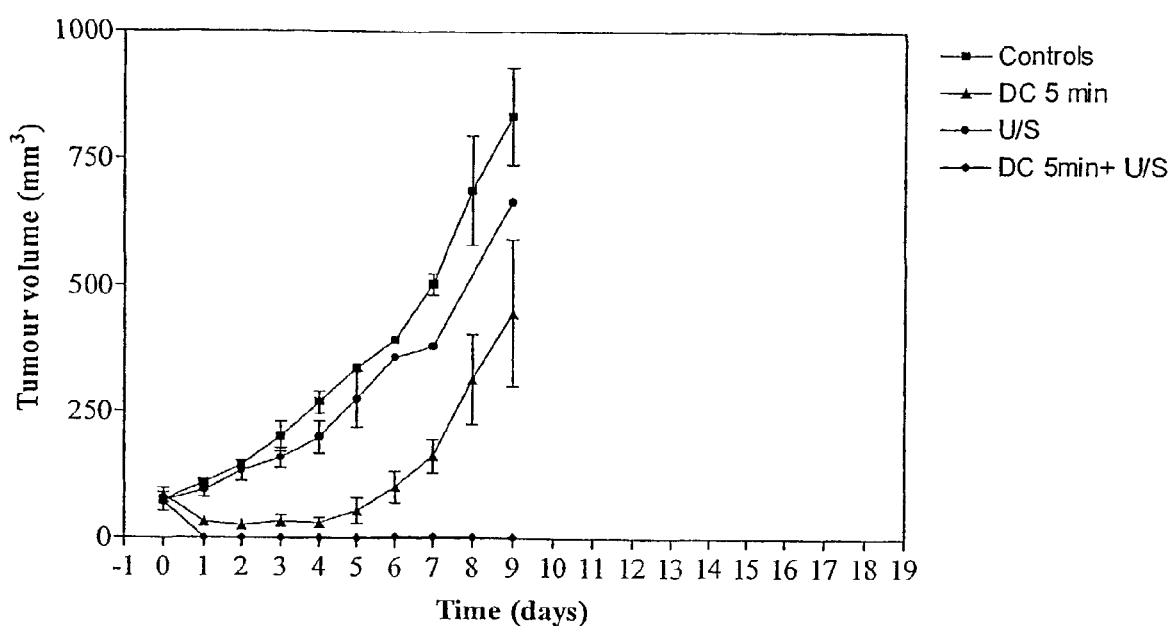
FIG. 13 shows the effect of treatment of RIF-1 tumours with ultrasound ( ), direct electric current ( ) and combined direct electric current with ultrasound ( ). Control animals are untreated ( ). Error bars represent ± SEM where n=2.

The results are shown in FIG. 13 and they demonstrate that treatment with direct electric current leads to a decrease in tumour volume, although this begins to increase again at days 4 to 5. Treatment with ultrasound has a slight effect on tumour growth although at no stage is a reduction in tumour volume detected. In the group of animals receiving the combined treatment with direct current and ultrasound, complete regression is observed and this continues to be the case within the time period examined. The results again demonstrate that combined treatment of tumours with direct electric current and ultrasound leads to dramatic tumour regression.

Example 14

Treatment of Tumours with Direct Current Together with Ultrasound (Six Animals)

The intention in this series of experiments described in this Example is to confirm the result obtained in the previous Example (DC treatment) and to examine the fate of animals receiving combined treatments over an extended period of time. In this case 6 animals are used in each group and both the DC and ultrasound treatments are similar to those described in Example 13. After treatment, tumour growth is measured in each group as described previously.

Example 14

Results

Figure 14:
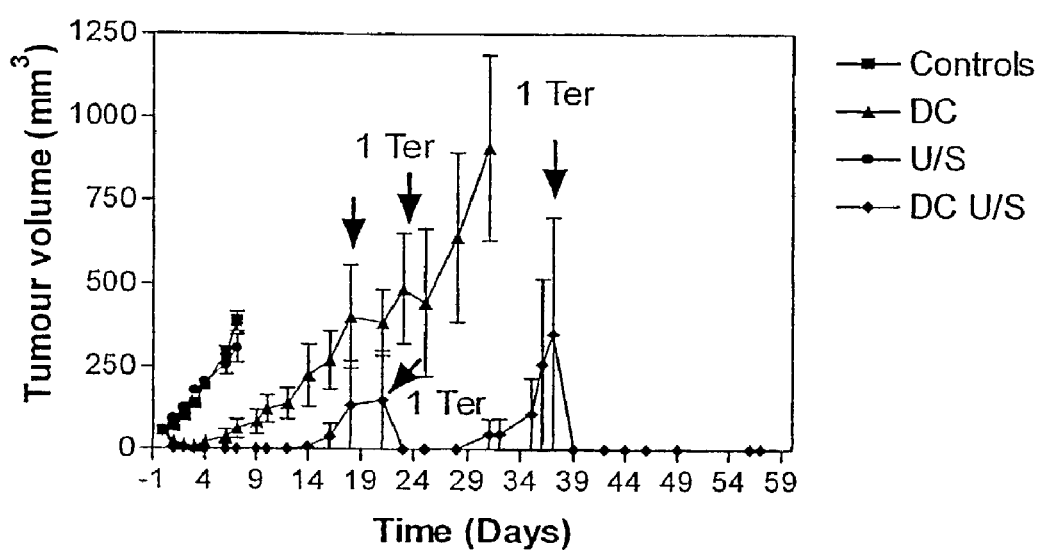
FIG. 14 is a graph showing results of treatment of tumours with ultrasound 22 hours after sensitisation with direct current (DC). Each group consists of 4 animals and groups are treated with direct current alone ( ), ultrasound alone ( ) and direct current followed, 22 hours later, by ultrasound ( ). Control animals ( ) receive no treatment. The bold arrow insets with 'Ter' indicate removal of animals from the experiment. Error bars represent +/− SEM (standard error mean).

The results obtained are shown in FIG. 14 and they demonstrate again, that a significant reduction in tumour growth is observed when animals are treated with the electric field alone. In this case the tumour mass is eradicated following treatment, although growth begins to appear in all animals after day 4.

In the group receiving combined ultrasound and electric field treatment the tumour masses are again eradicated. When this group of animals is monitored for a prolonged period of time three animals begin to exhibit growth at around day 14 and these animals are eventually sacrificed at day 23. On day 27 two further animals begin to exhibit measurable growth and these are terminated on day 35. Subsequently, the one remaining animal fully recovers and remains disease free throughout the period of time indicated in FIG. 14. Although five out of six animals exhibit tumour growth following combined treatment, the survival of one disease-free animal demonstrates that this approach can be used in the treatment of aggressive disease.

Example 15

Ultrasound Treatment of Tumours 22 Hours after Direct Current Treatment

In previous experiments it is demonstrated that treating tumours with ultrasound at extended times after delivery of the electric pulses yields an increased effect in terms of retarding tumour growth. In order to determine whether or not this applies to treatment with DC, animals with tumours are treated with DC (5 mA for 5 min.) and allowed to rest for a period of 22 hours. At this stage animals receiving the combined treatments are exposed to ultrasound (5 W/cm$^2$@1 MHz for 2 min. and pulsed at 35% continuous wave). In these experiments four animals are employed per group and tumour growth is monitored following treatment as described above.

Example 15

Results

Figure 15:
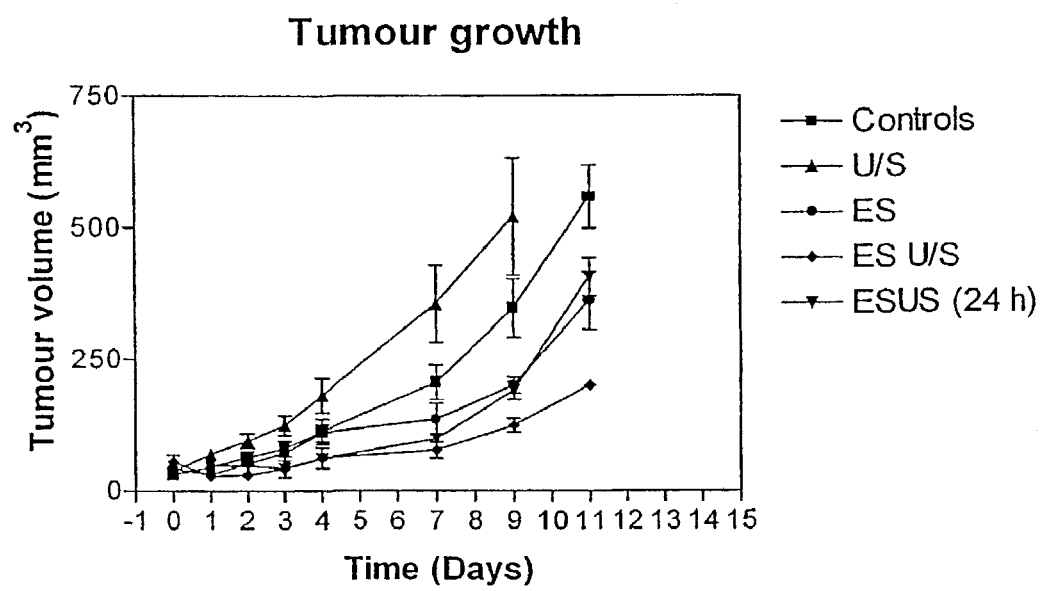
FIG. 15 is a graph showing sensitisation of tumours to ultrasound using high-intensity, short-duration square wave electric pulses. Each group consists of 4 animals and each group is treated with electric pulses alone ( ), ultrasound alone ( ), electric field treatment followed 24 hours later by ultrasound ( ) and electric field treatment followed immediately by ultrasound ( ) Control animals ( ) receive no treatment. Error bars represent +/− SEM (standard error mean).

The results from these experiments are shown in FIG. 15 and they again confirm a significant effect of DC treatment on tumour growth. However, as before, tumours begin to reappear in these animals after day 4. In the group receiving the DC treatment followed by ultrasound treatment at 22 h, the tumour masses are again completely eradicated. When these animals are monitored, growth in one animal appears after day 14 and this animal is terminated at day 20. Growth appears in another animal from this group after day 30 and this is terminated on day 37. In this group of animals receiving the combined treatment, two animals out of 4 remain disease-free throughout the duration of the experiment.

These results demonstrate the positive effects of DC treatment combined with ultrasound in terms of tumour eradication. In addition, the results also demonstrate that tumour cells remaining after the DC treatment remain sensitive to ultrasound in vivo for at least 22 hours.

FURTHER ASPECTS

Further aspects of the invention are now set out in the following numbered paragraphs; it is to be understood that the invention encompasses these aspects:

Paragraph 1. Use of an electric field to sensitise a nucleated cell to ultrasound.

Paragraph 2. Use of ultrasound to selectively disrupt a nucleated cell which has previously been electrosensitised by exposure to an electric field.

Paragraph 3. The combined use of an electric field and ultrasound to selectively ablate a cell or tissue.

Paragraph 4. Use according to any of Paragraphs 1, 2 or 3, in which the cell or tissue is electrosensitised by exposure to an electric field such that the cell or tissue is rendered more susceptible to disruption by exposure to a stimulus than n cell or tissue which has not been so electrosensitised.

Paragraph 5. Use according to any of Paragraphs 1 to 4, in which the cell or tissue is disrupted by exposure to ultrasound at a frequency and energy sufficient to cause disruption of the electrosensitised cell or tissue but insufficient to cause disruption of unsensitised cells or tissues.

Paragraph 6. A method for selectively ablating a cell or a tissue, the method comprising the steps of: (a) exposing the cell or tissue to an electric field to electrosensitise it; and (b) causing disruption of the electrosensitised cell by applying ultrasound at a frequency and energy sufficient to cause disruption of the electrosensitised cell but insufficient to cause disruption of unsensitised cells.

Paragraph 7. Use according to any of Paragraphs 1 to 5, or a method according to Paragraph 6, in which the cell is part of a tissue mass and a proportion of the tissue is electrosensitised.

Paragraph 8. A use or a method according to any preceding paragraph, in which the cell, tissue or tissue mass is comprised in an organism.

Paragraph 9. A use or a method according to any preceding paragraph, in which the tissue or tissue mass is a tumour tissue.

Paragraph 10. A use or a method according to any preceding paragraph, in which the cell disruption or cell or tissue ablation is a result of apoptosis of the cell, tissue or tissue mass.

Paragraph 11. A use or a method according to any preceding paragraph, in which the cell, tissue or tissue mass is exposed to an agent which is capable of facilitating cell death.

Paragraph 12. A use or a method according to any preceding paragraph, in which the cell death facilitating agent is selected from the group consisting of an oligonucleotide, a ribozyme, an antibody, and enzyme, a cytotoxic agent, a cytostatic agent, a cytokine, GM-CSF, IL-2, an immunogen, and combinations thereof.

Paragraph 13. A use or a method according to any preceding paragraph, in which the electric field is from about 1 Volt/cm to about 10 kVolts/cm under in vivo conditions.

Paragraph 14. A use or a method according to any preceding paragraph, in which the electric field is applied for between 1 μs and 100 milliseconds.

Paragraph 15. A use or a method according to any preceding paragraph, in which the applied ultrasound is at a power level of from about $0.05W/cm^2$ to about $100W/cm^2$.

Paragraph 16. A use or a method according to any preceding paragraph, in which the applied ultrasound is selected from continuous wave ultrasound and pulsed wave ultrasound.

Paragraph 17. A method of inducing apoptosis in a cell, the method comprising exposing the cell to an electric field, and exposing the cell to ultrasound.

Paragraph 18. A method of identifying a gene product which is involved in an apoptotic process or in modulating such a process, the method comprising the steps of: (a) inducing apoptosis in a cell by exposing the cell to an electric field and ultrasound; and (b) detecting a gene product which is up-regulated, down-regulated, or otherwise modulated in expression.

Paragraph 19. A method of identifying a gene product which is involved in an apoptotic process or in modulating such a process, the method comprising the steps of: (a) modulating the function of a gene product, or a gene encoding the gene product, in a cell; (b) exposing the cell to an electric field; (c) exposing the cell to ultrasound; and (d) determining whether the gene or gene product modulation has an effect on apoptosis.

Paragraph 20. A method of identifying a molecule which is capable of modulating apoptosis of a cell, the method comprising the steps of: (a) contacting a cell with a candidate molecule; (b) exposing the cell to an electric field; (c) exposing the cell to ultrasound; and (d) determining whether apoptosis is modulated as a result of the contacting.

Paragraph 21. A gene or gene product identified by a method according to Paragraph 18 or 19, or a modulator of apoptosis identified by a method according to Paragraph 20.

Paragraph 21. A method or use according to any preceding paragraph, in which the ultrasound and the electric field are applied in any order.

Each of the applications and patents mentioned above, and each document cited or referenced in each of the foregoing applications and patents, including during the prosecution of each of the foregoing applications and patents ("application cited documents") and any manufacturer's instructions or catalogues for any products cited or mentioned in each of the foregoing applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention will now be further described by way of the following numbered paragraphs:

1. The combined use of an electric field and ultrasound to ablate a cell or tissue.

2. A use according to paragraph 1, in which the cell or tissue is sensitised by exposure to the electric field or to the ultrasound, such that the cell or tissue is rendered more susceptible to disruption by exposure to the other of the electric field and ultrasound than a cell or tissue which has not been so sensitised.

3. A use according to paragraph 2, in which the cell or tissue is exposed to the other of the electric field or ultrasound at a frequency and energy sufficient to cause disruption of the sensitised cell or tissue but insufficient to cause disruption of unsensitised cells or tissues.

4. A use according to any of paragraphs 1 to 3, in which the electric field sensitises the cell or tissue to subsequent exposure to ultrasound.

5. The use of ultrasound to disrupt a nucleated cell which has previously been electrosensitised by exposure to an electric field.

6. Use of an electric field for sensitising a nucleated cell to ultrasound.

7. A use according to any of paragraphs 1 to 3, in which the ultrasound sensitises the cell or tissue to subsequent exposure to an electric field.

8. The use of electricity to disrupt a nucleated cell which has previously been sensitised by exposure to ultrasound.

9. Use of ultrasound for sensitising a nucleated cell to electricity.

10. A method for ablating a cell or a tissue, the method comprising the steps of:
  (a) exposing the cell or tissue to an electric field to render it more susceptible to disruption by ultrasound than a cell or tissue which has not been so exposed; and
  (b) causing disruption of the exposed cell by applying ultrasound.

11. A method for ablating a cell or a tissue, the method comprising the steps of:
  (a) exposing the cell or tissue to an electric field to electrosensitise it; and
  (b) causing disruption of the electrosensitised cell by applying ultrasound at a frequency and energy sufficient to cause disruption of the electrosensitised cell.

12. Use according to any of paragraphs 1 to 9, or a method according to paragraph 10 or 11, in which the cell is part of a tissue mass and a at least a portion of the tissue is sensitised.

13. A use or a method according to any preceding paragraph, in which the cell, tissue or tissue mass is comprised in an organism.

14. A use or a method according to any preceding paragraph, in which the cell, tissue or tissue mass comprises an undesired cell, an undesired tissue, a diseased cell, a diseased tissue, a tumour cell, a tumour tissue, or an otherwise abnormal cell or tissue.

15. A use or a method according to any preceding paragraph, in which the cell disruption or cell or tissue ablation is a result of apoptosis of the cell, tissue or tissue mass.

16. A use or a method according to paragraph 15, in which the apoptosis is induced by exposure to high intensity, short duration, exponential pulses of electricity.

17. A use or a method according to any preceding paragraph, in which the electric field is applied in a continuous or pulsed manner 18. A use or a method according to any preceding paragraph, in which the electric field is from about 1 Volt/cm to about 10 kVolts/cm under in vivo conditions.

19. A use or a method according to any preceding paragraph, in which the electric field is applied to produce a current of between 100 µA to 200 mA, preferably between 1 mA and 10 mA.

20. A use or a method according to any preceding paragraph, in which the electric field is applied for between 1 µs and 500 milliseconds.

21. A use or a method according to any preceding paragraph, in which the electric field is applied to the cell, tissue or tissue mass at a field strength of between 1V/cm and 20V/cm, for a period of 100 milliseconds or more, preferably 15 minutes or more.

22. A use or a method according to any preceding paragraph, in which the applied ultrasound is at a power level of from about $0.05W/cm^2$ to about $100W/cm^2$.

23. A use or a method according to any preceding paragraph, in which the applied ultrasound is selected from continuous wave ultrasound and pulsed wave ultrasound.

24. A use or a method according to any preceding paragraph, in which the cell, tissue or tissue mass is exposed to an agent which is capable of facilitating cell death.

25. A use or a method according to any preceding paragraph, in which the cell death facilitating agent is selected from the group consisting of an oligonucleotide, a ribozyme, an antibody, and enzyme, a cytotoxic agent, a cytostatic agent, a cytokine, GM-CSF, IL-2, an immunogen, a nucleic acid encoding any of the above, a cell producing or expressing any of the above, and combinations thereof.

26. A method of inducing apoptosis in a cell, the method comprising exposing the cell to an electric field, and exposing the cell to ultrasound.

27. A method of identifying a gene product which is involved in an apoptotic process or in modulating such a process, the method comprising the steps of:
   (a) inducing apoptosis in a cell by exposing the cell to an electric field and ultrasound; and
   (b) detecting a gene product which is up-regulated, down-regulated, or otherwise modulated in expression.

28. A method of identifying a gene product which is involved in an apoptotic process or in modulating such a process, the method comprising the steps of:
   (a) modulating the function of a gene product, or a gene encoding the gene product, in a cell;
   (b) exposing the cell to an electric field;
   (c) exposing the cell to ultrasound; and
   (d) determining whether the gene or gene product modulation has an effect on apoptosis.

29. A method of identifying a molecule which is capable of modulating apoptosis of a cell, the method comprising the steps of:
   (a) contacting a cell with a candidate molecule;
   (b) exposing the cell to an electric field;
   (c) exposing the cell to ultrasound; and
   (d) determining whether apoptosis is modulated as a result of the contacting.

30. A gene or gene product identified by a method according to paragraph 27 or 28, or a modulator of apoptosis identified by a method according to paragraph 28.

31. A method or use according to any preceding paragraph, in which the ultrasound is applied to the cell after the electric field.

32. A nucleated cell which has been exposed to ultrasound or an electric field to render it sensitive to disruption by a stimulus.

33. A nucleated cell which is rendered sensitive to disruption by ultrasound, as a result of exposure of the cell to an electric field.

34. A nucleated cell which is rendered sensitive to disruption by electricity, as a result of exposure of the cell to ultrasound.

The invention claimed is:

1. A method of using an electric field and ultrasound in combination to ablate a nucleated cell of a multicellular organism, comprising the steps of:
   (a)(i) sensitizing the cell by exposure to the ultrasound so that the cell is rendered more susceptible to disruption by exposure to the electric field than a cell which has not been so sensitized, and
   (b)(i) exposing said sensitized cell to the electric field,
      wherein the method begins with step (a)(i), and step (a)(i) is followed by step (b)(i), or
   (a)(ii) sensitizing the cell by exposure to the electric field so that the cell is rendered more susceptible to disruption by exposure to the ultrasound than a cell which has not been so sensitized, and
   (b)(ii) exposing said sensitized cell to the ultrasound,
      wherein the method begins with step (a)(ii), and step (a)(ii) is followed by step (b)(ii),
   whereby the cell is ablated.

2. The method of claim 1, wherein in step (b)(i) the cell is exposed to the electric field or in step (b)(ii) the cell is exposed to the ultrasound at a frequency and energy sufficient to cause disruption of the sensitised cell but insufficient to cause disruption of unsensitised cells.

3. The method of claim 1, wherein the method comprises the steps of:
   (a)(i) sensitizing the cell by exposure to the ultrasound so that the cell is rendered more susceptible to disruption by exposure to the electric field than a cell which has not been so sensitized, and
   (b)(i) exposing said sensitized cell to the electric field,
      wherein the method begins with step (a)(i), and step (a)(i) is followed by step (b)(i),
   whereby the cell is ablated.

4. The method of claim 3, wherein the method additionally comprises
   (a)(ii) sensitizing the cell by exposure to the electric field so that the cell is rendered more susceptible to disruption by exposure to the ultrasound than a cell which has not been so sensitized, and
   (b)(ii) exposing said sensitized cell to the ultrasound,
      wherein the method begins with step (a)(ii), and step (a)(ii) is followed by step (b)(ii),
   whereby the cell is ablated.

5. The method of claim 1, wherein the cell is part of a tissue mass and at least a portion of the tissue is sensitised.

6. The method of claim 5, wherein the tissue or tissue mass is exposed to an agent which is capable of facilitating cell death.

7. The method of claim 6, wherein the cell death facilitating agent is selected from the group consisting of an oligonucleotide, a ribozyme, an antibody, and enzyme, a cytotoxic agent, a cytostatic agent, a cytokine, GM-CSF, IL-2, an immunogen, a nucleic acid encoding any of the above, a cell producing or expressing any of the foregoing cell death facilitating agents, and combinations thereof.

8. The method of claim 1, wherein the cell is in an organism.

9. The method of claim 1, wherein the cell ablation is a result of apoptosis of the cell.

10. The method of claim 9, wherein the apoptosis is induced by exposure to high intensity, short duration, exponential pulses of electricity.

11. The method of claim 1, wherein the electric field is applied in a continuous or pulsed manner.

12. The method of claim 1, wherein the electric field is from about 1 Volt/cm to about 10 kVolts/cm under in vivo conditions.

13. The method of claim 1, wherein the electric field is applied to produce a current of between 100 µA to 200 mA.

14. The method of claim 13, wherein the electric field is applied to produce a current of between 1 mA and 10 mA.

15. The method of claim 1, wherein the electric field is applied for between 1 µs and 500 milliseconds.

16. The method of claim 1, wherein the electric field is applied to the cell at a field strength of between 1V/cm and 20V/cm, for a period of 100 milliseconds or more.

17. The method of claim 16 wherein the electric field is applied for 15 minutes or more.

18. The method of claim 1, wherein the applied ultrasound is at a power level of from about 0.05 $W/cm^2$ to about 100 $W/cm^2$.

19. The method of claim 1, wherein the applied ultrasound is selected from continuous wave ultrasound and pulsed wave ultrasound.

20. The method of claim 1 wherein the cell ablation is apoptosis and the method is a method of inducing apoptosis in a cell.

21. The method of claim 1 wherein the cell ablation is apoptosis and the method additionally comprises identifying a gene product which is involved in an apoptotic process or in modulating such a process.

22. The method of claim 21, wherein the identifying of a gene product which is involved in an apoptotic process or in modulating such a process comprises
    detecting a gene product which is up-regulated, down-regulated, or otherwise modulated in expression.

23. The method of claim 21, wherein the identifying a gene product further comprises
    modulating the function of a gene product, or a gene encoding the gene product, in a cell;
    determining whether the gene or gene product modulation has an effect on apoptosis.

24. The method of claim 1 wherein the cell ablation is apoptosis and the method further comprises identifying a molecule which is capable of modulating apoptosis of a cell comprising
    contacting the cell with a candidate molecule and
    determining whether apoptosis is modulated as a result of the contacting.

25. The method of claim 1 wherein the cell is a tumour cell.

26. The method of claim 25 wherein the cell is a part of tumour tissue.

27. The method of claim 1 wherein the cell comprises an undesired cell, a diseased cell, a tumour cell or an otherwise abnormal cell.

28. The method of claim 1, wherein the method comprises
    (a)(ii) sensitizing the cell by exposure to the electric field so that the cell is rendered more susceptible to disruption by exposure to the ultrasound than a cell which has not been so sensitized, and
    (b)(ii) exposing said sensitized cell to the ultrasound,
        wherein the method begins with step (a)(ii), and step (a)(ii) is followed by step (b)(ii),
    whereby the cell is ablated.

* * * * *